United States Patent
Bowler et al.

(10) Patent No.: US 12,275,985 B2
(45) Date of Patent: Apr. 15, 2025

(54) REDOX LABELED OLIGONUCLEOTIDE PROBES AND THEIR USE

(71) Applicant: ABBOTT DIAGNOSTICS SCARBOROUGH, INC., Scarborough, ME (US)

(72) Inventors: Frank Ray Bowler, Norfolk (GB); Grzegorz Artur Orlowski, Cambridgeshire (GB); Hazel Lucy Greetham, Cambridgeshire (GB); Cheng Zhou, Cambridgeshire (GB); Niall A. Armes, Suffolk (GB); Olaf Piepenburg, Essex (GB)

(73) Assignee: ABBOTT DIAGNOSTICS SCARBOROUGH, INC., Scarborough, ME (US)

( * ) Notice: Subject to any disclaimer, the term of this patent is extended or adjusted under 35 U.S.C. 154(b) by 0 days.

(21) Appl. No.: 18/317,200

(22) Filed: May 15, 2023

(65) Prior Publication Data
US 2024/0052399 A1    Feb. 15, 2024

Related U.S. Application Data

(62) Division of application No. 16/079,273, filed as application No. PCT/US2017/019446 on Feb. 24, 2017, now Pat. No. 11,649,484.

(60) Provisional application No. 62/300,242, filed on Feb. 26, 2016.

(51) Int. Cl.
| | | |
|---|---|---|
| C12Q 1/68 | (2018.01) | |
| C07H 21/04 | (2006.01) | |
| C12P 19/34 | (2006.01) | |
| C12Q 1/6816 | (2018.01) | |
| C12Q 1/6825 | (2018.01) | |
| C12Q 1/6876 | (2018.01) | |

(52) U.S. Cl.
CPC ........... *C12Q 1/6825* (2013.01); *C07H 21/04* (2013.01); *C12P 19/34* (2013.01); *C12Q 1/6816* (2013.01); *C12Q 1/6876* (2013.01)

(58) Field of Classification Search
CPC .. C12Q 1/6825; C12Q 1/6816; C12Q 1/6876; C12P 19/34; C07H 21/04
See application file for complete search history.

(56) References Cited

U.S. PATENT DOCUMENTS

| | | |
|---|---|---|
| 6,134,461 A | 10/2000 | Say et al. |
| 7,270,981 B2 | 9/2007 | Armes et al. |
| 7,399,590 B2 | 7/2008 | Piepenburg et al. |

(Continued)

FOREIGN PATENT DOCUMENTS

| | | |
|---|---|---|
| EP | 1481083 | 12/2004 |
| EP | 1808494 | 7/2007 |

(Continued)

OTHER PUBLICATIONS

Li et al., "Advances in Isothermal Amplification: Novel Strategies Inspired by Biological Processes," Biosens Bioelectron, vol. 64, Feb. 15, 2015, pp. 196-211.

(Continued)

*Primary Examiner* — Jezia Riley
(74) *Attorney, Agent, or Firm* — Casimir Jones, S.C.; Thomas A. Isenbarger

(57) ABSTRACT

This invention relates to sequence specific electrochemically-labeled oligonucleotide probes for the detection of nucleic acids and methods associated therewith.

17 Claims, 13 Drawing Sheets

Specification includes a Sequence Listing.

(56) References Cited

U.S. PATENT DOCUMENTS

| | | |
|---|---|---|
| 7,435,561 B2 | 10/2008 | Piepenburg et al. |
| 7,666,598 B2 | 2/2010 | Piepenburg et al. |
| 8,071,308 B2 | 12/2011 | Piepenburg et al. |
| 8,580,507 B2 | 11/2013 | Piepenburg et al. |
| 2003/0175785 A1 | 9/2003 | Patel et al. |
| 2003/0232354 A1 | 12/2003 | Yu et al. |
| 2004/0086892 A1 | 5/2004 | Crothers et al. |
| 2009/0017453 A1 | 1/2009 | Maples et al. |
| 2009/0029421 A1 | 1/2009 | Piepenburg et al. |
| 2009/0081670 A1 | 3/2009 | Maples et al. |
| 2011/0053153 A1 | 3/2011 | Piepenburg et al. |
| 2012/0258456 A1 | 10/2012 | Armes et al. |
| 2013/0109577 A1 | 5/2013 | Korlach et al. |
| 2015/0024397 A1 | 1/2015 | Armes et al. |

FOREIGN PATENT DOCUMENTS

| | | |
|---|---|---|
| WO | 2010135310 | 11/2010 |
| WO | 2010141940 | 12/2010 |
| WO | 2011014645 | 2/2011 |
| WO | 2012/085591 | 6/2012 |

OTHER PUBLICATIONS

Lin et al., "Origins and evolution of the recA/RAD51 gene family: evidence for ancient gene duplication and endosymbiotic gene transfer." Proc Natl Acad Sci U S A. Jul. 5, 2006;103(27):10328-10333.

Ming et al., "Integrated Quantum Dot Barcode Smartphone Optical Devices for Wireless Multiplexed Diagnosis of Infected Patients," ACS Nano, vol. 9, No. 3, 2015, pp. 3060-3074.

International Search Report in corresponding International Application No. PCT/US2017/019446, 4 pages.

Hocek, M. et al. Nucleobase modification as redox DNA labelling for electrochemical detection. Chem Soc Rev. Dec. 2011;40(12):5802-14.

Kersting, S. et al. Multiplex isothermal solid-phase recombinase polymerase amplification for the specific and fast DNA-based detection of three bacterial pathogens. Mikrochim Acta. 2014;181(13-14):1715-1723.

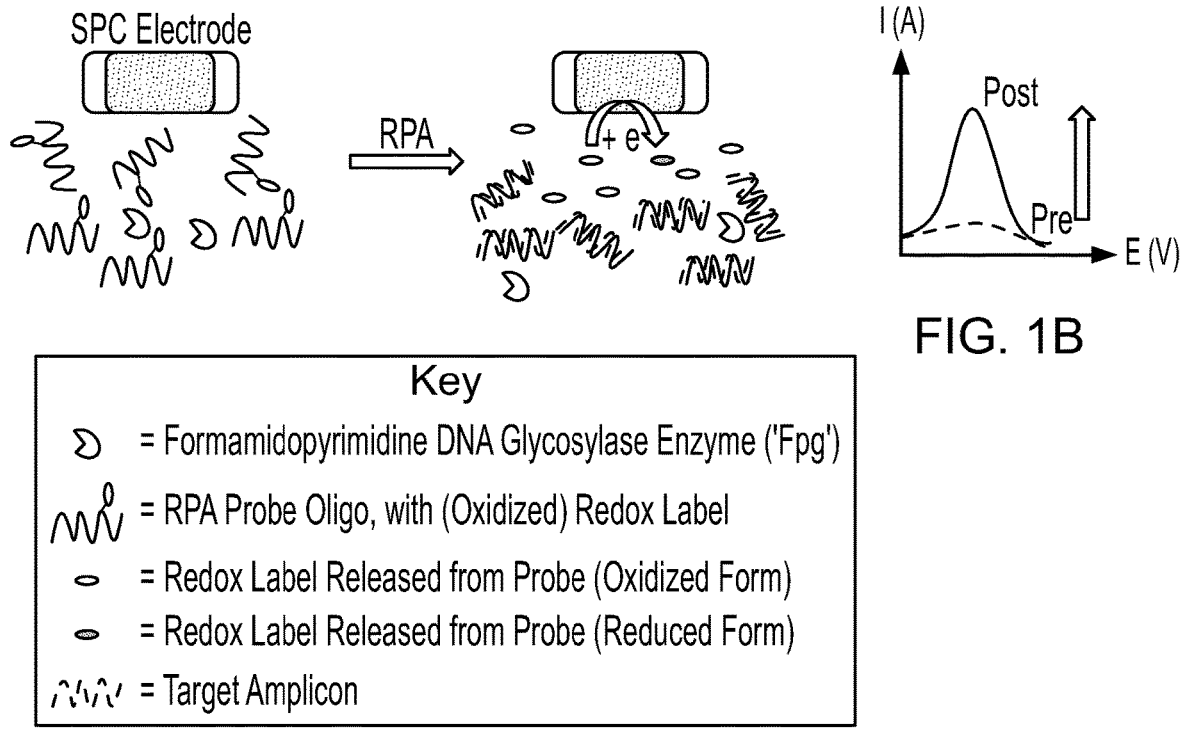
FIG. 1A
FIG. 1B
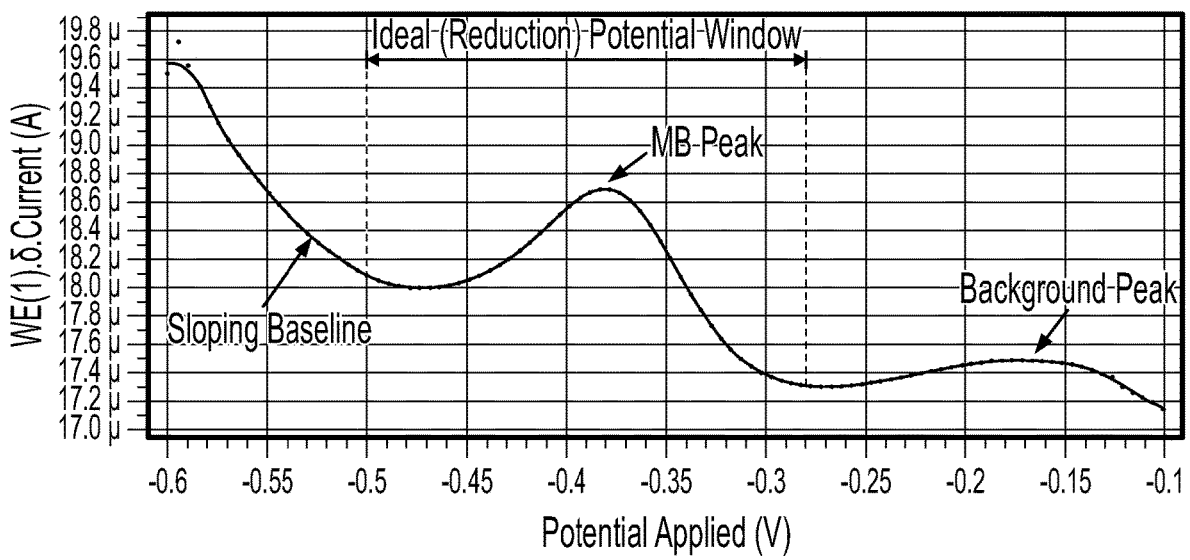
FIG. 2

Fpg Probes:

Methlene Blue

Nile Blue

Anthraquinone-2-amidopentyl Carboxylic Acid ('AQ(C6)')

REDOX LABELED OLIGONUCLEOTIDE PROBES AND THEIR USE

RELATED APPLICATIONS

This application is a divisional of U.S. application Ser. No. 16/079,273, filed Aug. 23, 2018, now U.S. Pat. No. 11,649,484, issued May 16, 2023, which is a national phase application under 35 U.S.C. § 371 of PCT International Application No. PCT/US2017/019446, filed Feb. 24, 2017, which claims the benefit of priority to U.S. Patent Application Ser. No. 62/300,242 filed Feb. 26, 2016, which is hereby incorporated by reference in its entirety.

STATEMENT OF GOVERNMENT INTEREST

This invention was made with Government support under HHSO100201400011C awarded by the U.S. Department of Health and Human Services. The government has certain rights in the invention.

SEQUENCE LISTING

The computer readable sequence listing filed herewith, titled "35629-403 SQL", created May 15, 2023, having a file size of 28,955 bytes, is hereby incorporated by reference in its entirety.

TECHNICAL FIELD

This document relates to compositions and methods for detection of nucleic acids. More specifically, this document relates to sequence specific electrochemically labeled oligonucleotide probes for the detection of nucleic acids and methods associated therewith.

BACKGROUND

Detection of trace levels of target nucleic acids can play a significant role in the detection of pathogens and genetic disease and with helping to tailor treatment regimens to particular infections or genotypes. Certain isothermal nucleic acid amplification methods are able to amplify target nucleic acid from trace levels to very high and detectable levels within a matter of minutes. Such isothermal methods, e.g., Recombinase Polymerase Amplification (RPA) or Nicking and Extension Amplification Reaction (NEAR), can allow users to detect and quantify a particular sequence in trace amounts, facilitating point-of-care testing and increasing the accessibility and speed of diagnostics.

SUMMARY

The present disclosure is based, at least in part, on the development of oligonucleotide probes, compositions comprising the oligonucleotide probes, and methods of use thereof for monitoring (i.e., detecting, quantifying) a target nucleic acid sequence. The oligonucleotide probes disclosed herein have several advantages including, for example, providing an accurate, sensitive and reproducible platform In one aspect, the disclosure features an oligonucleotide probe comprising one or more modified residues, e.g., a modified internal residue, conjugated to a redox moiety and a 3' blocking group to prevent polymerase extension. The one or more modified residues can be, for example, an abasic residue, tetrahydrofuran (d-spacer), or a dR-O—[C]n nucleotide that lacks a base and has a sugar with a carbon at a 1' position, and wherein the carbon at the 1' position is covalently linked through an oxygen atom to a carbon atom of a linker containing n carbon atoms, in which the linker is conjugated to the redox moiety.

In some embodiments, the redox moiety can be a phenothiazine, a phenoxazine, a ferrocene, ruthenium (II), osmium (II), an anthraquinone, a phenazine, or derivatives thereof. For example, the redox moiety can be a phenothiazine derivative consisting of methylene blue or PZ9 or one of the following structures:

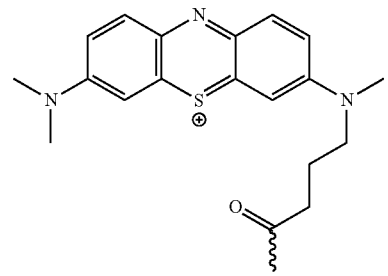

MB = Methylene Blue

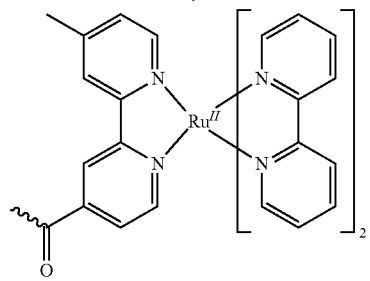

Ru(II) = [Ru(bpy)$_2$(mcbpy)]$^{2+}$

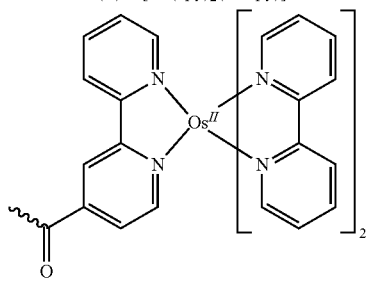

Os(II) = [Os(bpy)$_2$(cbpy)]$^{2+}$

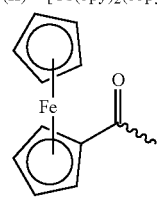

Fe = Ferrocene

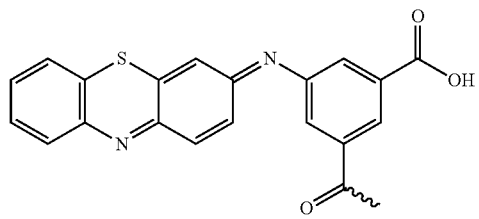

CP1 = 5((3H-Phenothiazin-3-ylidene)amino)isophthalic acid

3

-continued

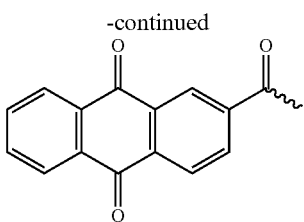

AQ = anthraquinone-2-carboxylic acid

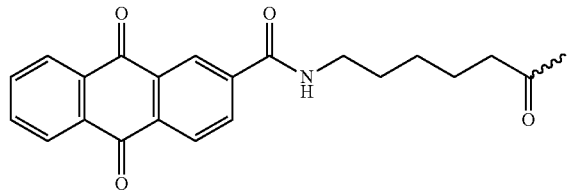

AQ(C6) = anthraquinone-2-amidopentyl carboxylic acid

4

-continued

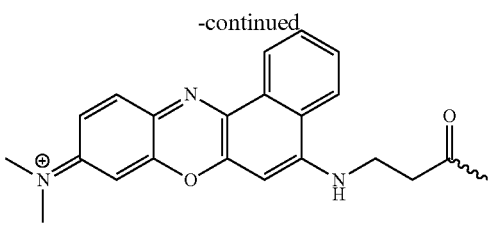

NB = Nile Blue

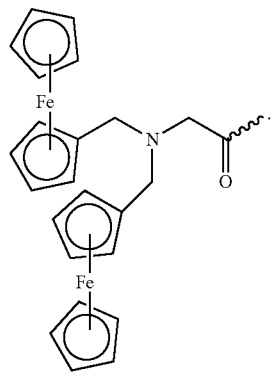

Di-Fc = di-ferrocene, or
N,N-(diferrocenylmethyl)glycine

The modified residue conjugated to the redox moiety can have the structure of:

Formula I

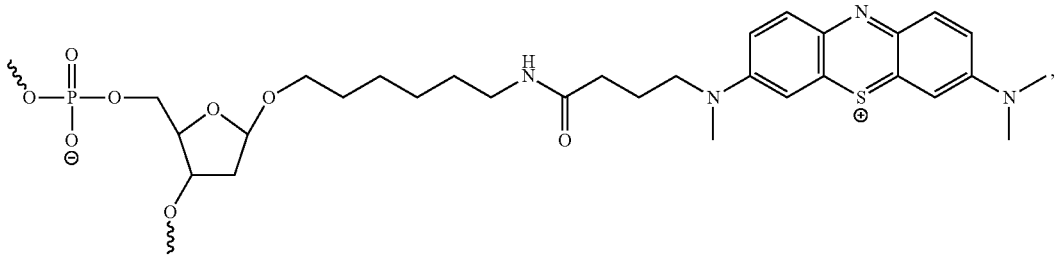

Methylene Blue

Formula II

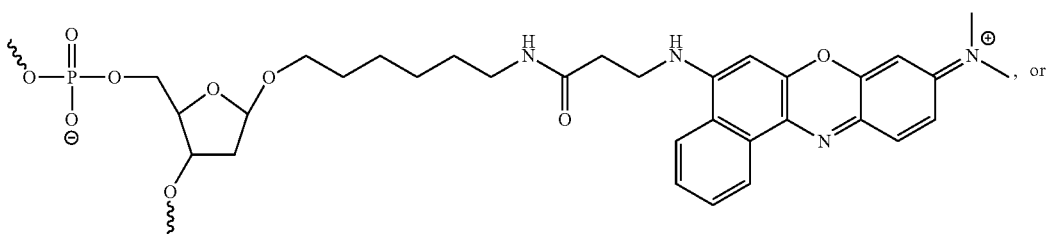

Nile Blue

Formula III

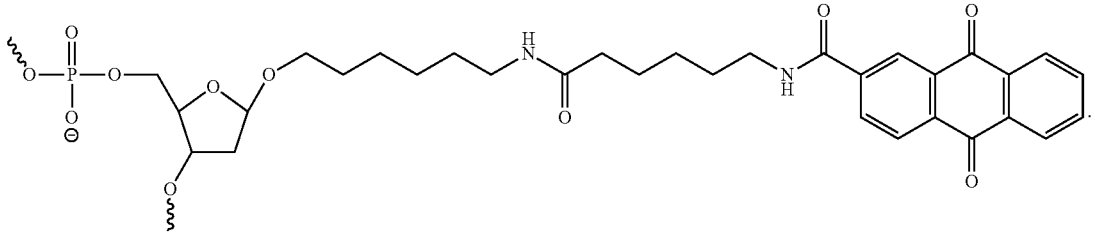

Anthraquinone-2-amidopentyl carboxylic acid
('AQ(C6)')

In some embodiments, the modified residue conjugated to a redox moiety has a structure selected from the group consisting of:

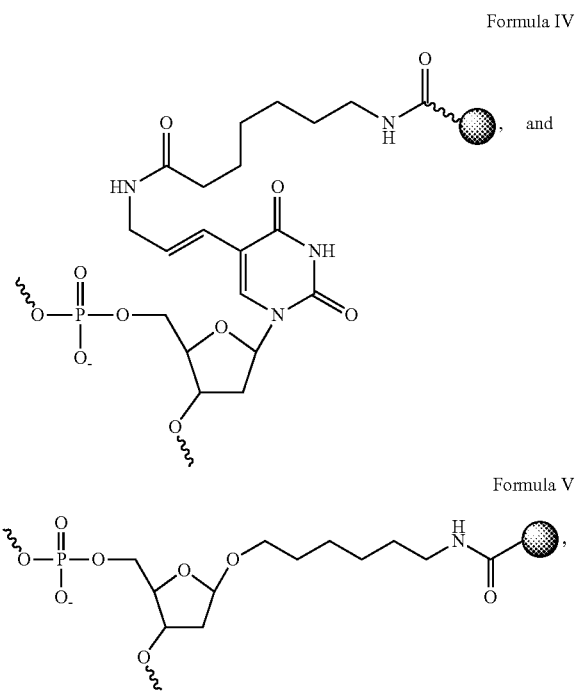

wherein

represents a redox moiety.

In some aspects, the disclosure features an oligonucleotide probe comprising a 3' blocking group to prevent polymerase extension.

In some aspects, the disclosure features an oligonucleotide probe comprising one or more modified internal residues, e.g., a modified internal residue, conjugated to a redox moiety and a 3' blocking group to prevent polymerase extension.

In some embodiments, the oligonucleotide probe comprises a nucleic acid sequence of AAGCAATTGAG-GAGTGCCTGATTAAT[dR-RM]ATCCCTGGGTTTTG (SEQ ID NO:1); GTCTGGCTGTCAGTAAGTAT[dR-RM]CTAGAGTCCCGTTTT (SEQ ID NO: 2); TCAGCTA-CAATCAAGACTACTCGTTAA[dR-RM]TAATGAATC-CTCA (SEQ ID NO: 3); or GCACACTTGTCACCTACAT-TTCTGATT[dR-RM]GTGGACTCTAACAT (SEQ ID NO: 4), wherein dR-RM represents a deoxyribonucleotide conjugated to RM, wherein RM represents a redox moiety.

In some embodiments, the oligonucleotide probe comprises a nucleic acid sequence of CATCAGCTTTTG-GAGCTTGAGAGTCAT[T(methylene blue)]A[dSpacer]G-TTTTTGAGCTTCAC (SEQ ID NO: 5), GAACCAA-GAAGCATTRAGCAAAACCCAGGGA[T(methylene blue)][dSpacer]ATTAATCAGGCACTC (SEQ ID NO: 6), or ACTGATGATATTCAGC[T(methylene blue)]ACAA[T(methylene blue)]CAAGAC[T(methylene blue)]A[dSpacer] TCGTTAAGTAATGAA (SEQ ID NO: 7), wherein "dspacer" is an abasic site mimic.

In some embodiments, the oligonucleotide can comprise more than one modified residues, e.g, two or more, three or more, or four or more modified residues, wherein each modified residue is conjugated to a redox moiety. For example, in some embodiments, the oligonucleotide probe can comprise a first modified residue conjugated to a first redox moiety at a first internal site and a second modified residue conjugated to a second redox moiety at a second internal site. The first redox moiety and the second redox moiety can be the same, or different.

In some instances, the oligonucleotide probe is cleavable by a nuclease selected from the group consisting of AP endonuclease, DNA glycosylase/lyase and DNA glycosylase at the non-complementary or modified residue when the oligonucleotide probe is hybridized to a complementary nucleic acid sequence. The oligonucleotide probe can be, for example, 12 to 30, 12-40, or 12-60 residues in length.

In another aspect, the disclosure features a composition comprising an oligonucleotide probe as described herein and a nuclease. In some embodiments, the nuclease is capable of cleaving the oligonucleotide probe at the non-complementary or modified residue when hybridized to a complementary nucleic acid sequence. In some instances, the nuclease is selected from the group consisting of AP endonuclease, DNA glycosylase/lyase and DNA glycosylase. For example, the nuclease can be Fpg or ExoIII. The composition can be lyophilized.

In another aspect, the disclosure features a composition comprising an oligonucleotide probe as described herein, a recombinase agent, one or more nucleic acid primers, and a nuclease. In some embodiments, the nuclease is capable of cleaving the oligonucleotide probe at the non-complementary or modified residue when hybridized to a complementary nucleic acid sequence. In some instances, the nuclease is selected from the group consisting of AP endonuclease, DNA glycosylase/lyase and DNA glycosylase. For example, the nuclease can be Fpg or ExoIII. The composition can be lyophilized.

In another aspect, the disclosure features a method of identifying the presence or absence of a target nucleic acid sequence in a sample, the method comprising performing isothermal nucleic acid amplification on the sample to form a nucleic acid amplification mixture, contacting the nucleic acid amplification mixture with an oligonucleotide probe and at least one nuclease, wherein the oligonucleotide probe comprises a sequence complementary to the target polynucleotide sequence, one or more modified internal residues conjugated to a redox moiety, and a 3' blocking group to prevent polymerase extension, and identifying the presence or absence of a target nucleic acid sequence in a sample by electrochemically detecting a signal of a cleaved redox moiety, wherein a detectable signal is indicative of the presence of the target nucleic acid sequence.

The step of contacting the nucleic acid amplification mixture with an oligonucleotide probe and at least one nuclease can be performed by contacting the mixture with the oligonucleotide probe and the least one nuclease concurrently. The step of contacting the nucleic acid amplification mixture with an oligonucleotide probe and at least one nuclease can be performed by contacting the mixture with the oligonucleotide probe and the least one nuclease sequentially.

In some embodiments, the step of performing isothermal nucleic acid amplification is conducted in the presence of the nuclease and the oligonucleotide probe. In some instances, the nuclease is capable of cleaving the oligonucleotide probe at the modified internal residue when hybridized to a complementary target nucleic acid sequence. In some instances, the nuclease is not capable of cleaving the oligonucleotide probe unless hybridized to a complementary nucleic acid sequence.

Electrochemically detecting a signal can be performed using pulse voltammetry, amperometry, or impedance measurement.

In some embodiments, prior to cleavage of the oligonucleotide probe by the nuclease, the redox label does not generate an electrical current in response to the electrical potential applied across electrodes in contact with the nucleic acid amplification mixture.

In some embodiments of all aspects, the redox moiety can be a phenothiazine, a phenoxazine, a ferrocene, ruthenium (II), osmium (II), an anthraquinone, a phenazine, or derivatives thereof. For example the redox moiety can be a phenothiazine derivative such as methylene blue and PZ9.

In some embodiments, the modified residue conjugated to a redox moiety has a structure of:

In some embodiments of all aspects, the modified residue conjugated to a redox moiety has a structure of:

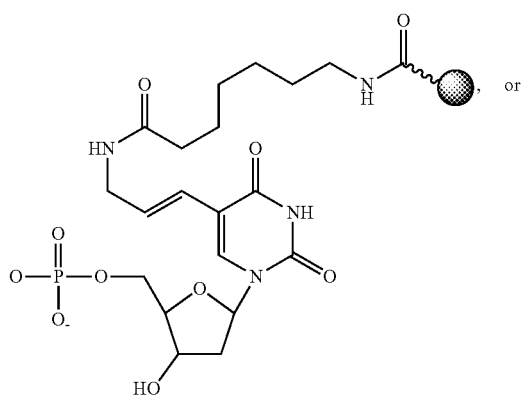

Formula IV

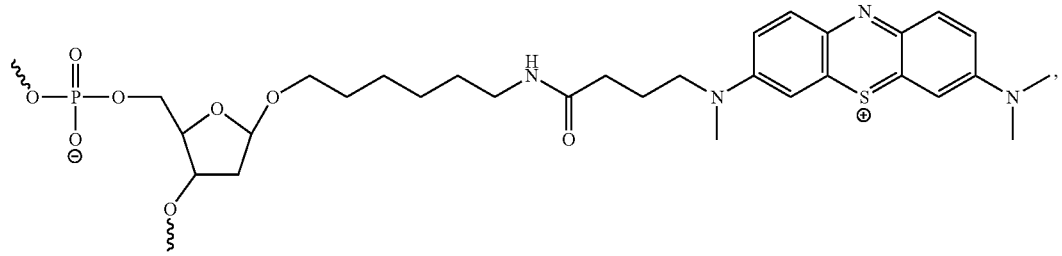

Formula I

Methylene Blue

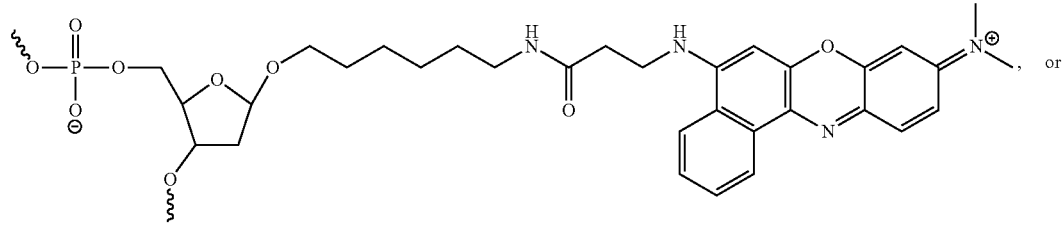

Formula II

Nile Blue

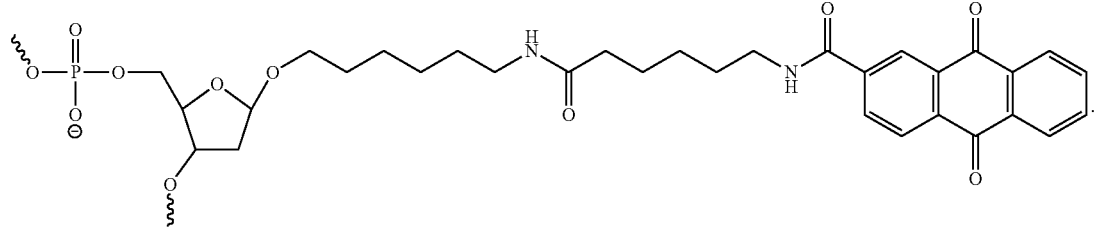

Formula III

Anthraquinone-2-amidopentyl carboxylic acid ('AQ(C6)')

Formula V

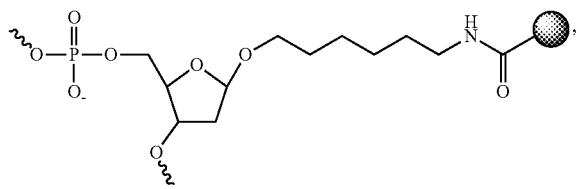

wherein

represents a redox moiety.

In some embodiments, the oligonucleotide probe comprises a nucleic acid sequence at least 90% identical to AAGCAATTGAGGAGTGCCTGATTAAT[dR-RM]ATC-CCTGGGTTTTG (SEQ ID NO:1), GTCTGGCTGT- CAG-TAAGTAT[dR-RM]CTAGAGTCCCGTTTT (SEQ ID NO: 2); TCAGCTACAATCAAGACTACTCGTTAA[dR-RM]T-AATGAATCCTCA (SEQ ID NO: 3); or GCACACTTGT-CACCTACATTTCTGATT[dR-RM]GTGGACTCTAACAT (SEQ ID NO: 4), wherein RM represents a redox moiety.

In some embodiments the oligonucleotide probe comprises a nucleic acid sequence that is at least 90% identical to CATCAGCTTTTGGAGCTTGAGAGTCAT[T(methylene blue)]A[dSpacer]GTTTTTGAGCTTCAC (SEQ ID NO: 5), GAACCAAGAAGCATTRAGCAAAACCCAGG-GA[T(methylene blue)][dSpacer]ATTAATCAGGCACTC (SEQ ID NO: 6), or ACTGATGATATTCAGC[T(methylene blue)]ACAA[T(methylene blue)]CAAGAC[T(methylene blue)]A[dSpacer]TCGTTAAGTAATGAA (SEQ ID NO: 7).

In some embodiments, the oligonucleotide probe comprises a first modified internal residue conjugated to a first redox moiety at a first internal site and a second modified internal residue conjugated to a second redox moiety at a second internal site. In some instances, the first redox moiety and the second redox moiety are the same, or are different.

In some embodiments, the oligonucleotide can have a nucleotide sequence substantially complementary to a *Streptococcus* gene sequence (e.g., *Streptococcus pyogenes* gene sequence), an Influenza A gene sequence, an Influenza B gene sequence, a *Campylobacter* gene sequence, a *Salmonella* gene sequence, a *Neisseria* gene sequence, a *Chlamydia* gene sequence, or a *Listeria* gene sequence.

In some embodiments, the oligonucleotide probe is cleavable by a nuclease selected from the group consisting of AP endonuclease, DNA glycosylase/lyase and DNA glycosylase at the non-complementary or modified residue when hybridized to a complementary nucleic acid sequence. The oligonucleotide probe can be 12 to 30, 12-40, or 12-60 residues in length.

In another aspect, the disclosure features a method comprising: contacting an oligonucleotide probe comprising a sequence complementary to the target polynucleotide sequence, one or more modified internal residues conjugated to a redox moiety, and a 3' blocking group to a target nucleic acid sequence with a nucleic acid amplification mixture; contacting the mixture with a nuclease; and electrochemically detecting a signal from the cleaved redox moiety, wherein a detectable signal is indicative of the presence of the target nucleic acid sequence.

In some embodiments, the nuclease is capable of cleaving the oligonucleotide probe at the non-complementary or modified residue when hybridized to a complementary nucleic acid sequence. In some instances, the nuclease is not capable of cleaving the oligonucleotide probe unless hybridized to a complementary nucleic acid sequence.

In some instances, electrochemically detecting a signal is performed using differential pulse voltammetry, amperometry, or impedance measurement. In some embodiments, prior to cleaving the oligonucleotide probe, the redox label does not generate an electrical current in response to the electrical potential applied across electrodes in contact with the reaction mixture.

The modified internal residue can be an abasic residue, tetrahydrofuran (d-spacer), or a dR-O—[C]n nucleotide that lacks a base and has a sugar with a carbon at a 1' position, and wherein the carbon at the 1' position is covalently linked through an oxygen atom to a carbon atom of a linker containing n carbon atoms, in which the linker is conjugated to the redox moiety.

The redox moiety can be a phenothiazine, a phenoxazine, a ferrocene, ruthenium (II), osmium (II), an anthraquinone, a phenazine, or derivatives thereof. In some embodiments, the redox moiety is a phenothiazine derivative selected from methylene blue or PZ9.

In some embodiments, the modified internal residue conjugated to a redox moiety has a structure selected from the group consisting of:

Formula I

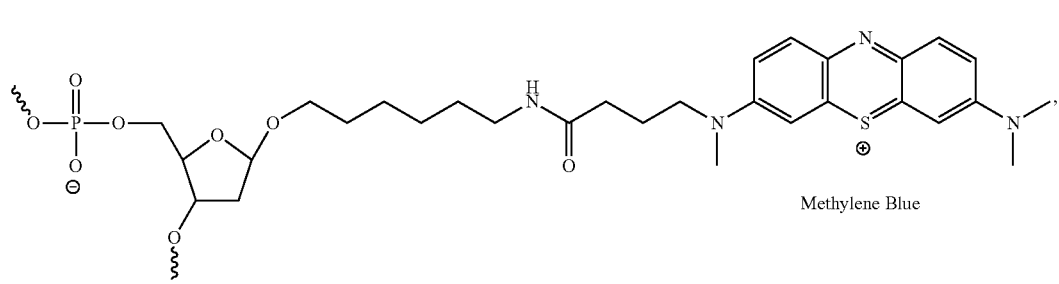

Methylene Blue

-continued

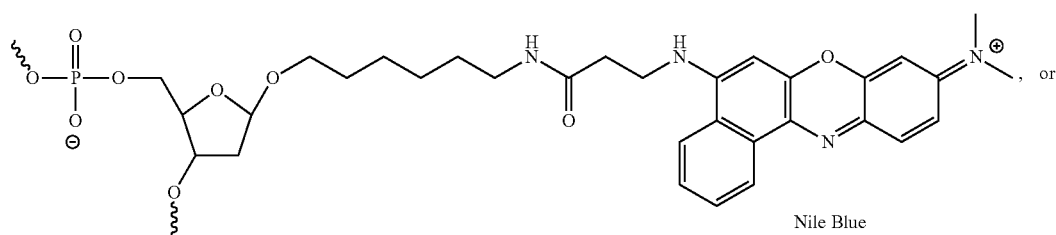

Formula II

Nile Blue

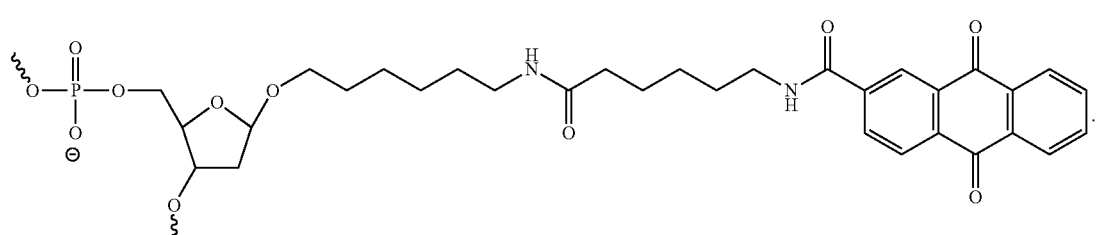

Formula III

Anthraquinone-2-amidopentyl carboxylic acid ("AQ(C6)")

The modified internal residue conjugated to a redox moiety can also have a structure of:

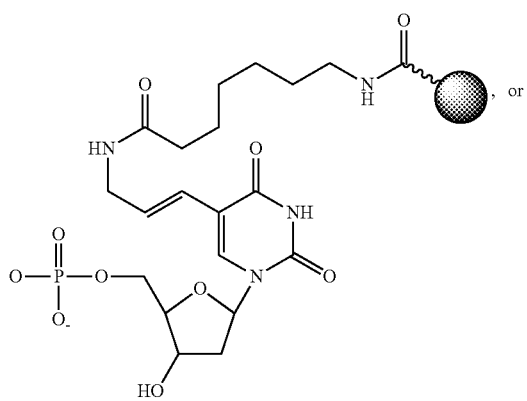

Formula IV

, or

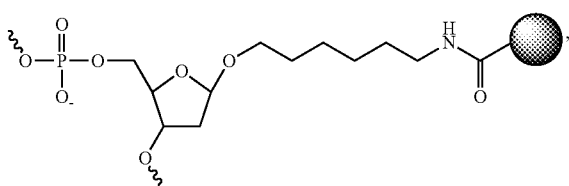

Formula V wherein

represents a redox moiety.

In some embodiments, the oligonucleotide probe comprises a nucleic sequence selected from the group consisting of nucleic acid sequences at least 90% identical to AAGCAATTGAGGAGTGCCTGATTAAT[dR-RM]ATC-CCTGGGTTTTG (SEQ ID NO:1), GTCTGGCTGT-CAGTAAGTAT[dR-RM]CTAGAGTCCCGTTTT (SEQ ID NO: 2); TCAGCTACAATCAAGACTACTCGTTAA[dR-RM]TAATGAATCCTCA (SEQ ID NO: 3); and GCAC-ACTTGTCACCTACATTTCTGATT[dR-RM]GTGGAC-TCTAACAT (SEQ ID NO: 4), wherein RM represents a redox moiety. In some embodiments, the oligonucleotide probe comprises a nucleic sequence selected from the group consisting of nucleic acid sequences at least 90% identical to CATCAGCTTTTGGAGCTTGAGAGTCAT[T(methylene blue)]A[dSpacer]GTTTTTGAGCTTCAC (SEQ ID NO: 5), GAACCAAGAAGCATTRAGCAAAACCCAGGGA[T (methylene blue)][dSpacer]ATTAATCAGGCACTC (SEQ ID NO: 6), and ACTGATGATATTCAGC[T(methylene blue)]ACAA[T(methylene blue)]CAAGAC[T(methylene blue)]A[dSpacer]TCGTTAAGTAATGAA (SEQ ID NO: 7).

In some embodiments, the oligonucleotide probe comprises a first modified residue conjugated to a first redox moiety at a first internal site and a second modified residue conjugated to a second redox moiety at a second internal site. In some instances, the first redox moiety and the second redox moiety are the same, or are different. In some embodiments, the oligonucleotide has a nucleotide sequence substantially complementary to a gene sequence of any of the organisms described herein, e.g., any of the bacteria, fungi, parasite, and/or viruses described herein. In some embodiments, the oligonucleotide has a nucleotide sequence substantially complementary to a Streptococcus gene sequence (e.g., Streptococcus pyogenes gene sequence), an Influenza A gene sequence, an Influenza B gene sequence, a Campylobacter gene sequence, a Salmonella gene sequence, a Neisseria gene sequence, a Chlamydia gene sequence, or a Listeria gene sequence.

In some embodiments, the oligonucleotide probe is cleavable by a nuclease selected from the group consisting of AP endonuclease, DNA glycosylase/lyase and DNA glycosylase at the non-complementary or modified residue when hybridized to a complementary nucleic acid sequence.

In another aspect, the disclosure provides a method comprising performing a first round of amplification on a target nucleic acid comprising a target polynucleotide sequence to form a first amplified polynucleotide product, performing a second round of amplification on the first amplified polynucleotide product to form a second amplified polynucleotide product comprising the target polynucleotide sequence, wherein the second amplified polynucleotide product comprises a smaller polynucleotide sequence completely contained within the first amplified polynucleotide product, contacting the second amplified polynucleotide product with a first oligonucleotide probe and a at least one nuclease, the first oligonucleotide probed comprising one or more internal non-complementary or modified residue conjugated to a redox moiety and having a sequence complementary to the target polynucleotide sequence to form a double stranded nucleic acid product, cleaving the redox moiety from the double stranded nucleic acid product; and electrochemically detecting a signal from the cleaved redox moiety, wherein a detectable signal is indicative of the presence of the second amplified polynucleotide product.

In another aspect, the disclosure provides a method comprising performing a first round of amplification on a target nucleic acid comprising a target polynucleotide sequence to form a first amplified polynucleotide product; performing additional successive rounds of amplification on the first amplified polynucleotide product to form additional amplified polynucleotide products, each product comprising the target polynucleotide sequence, wherein the amplified polynucleotide product from each successive n+1 round of amplification comprises a smaller polynucleotide sequence completely contained within the amplified polynucleotide product of the prior nth round; contacting the second amplified polynucleotide product with a first oligonucleotide probe and a at least one nuclease, the first oligonucleotide probed comprising one or more internal non-complementary or modified residue conjugated to a redox moiety and having a sequence complementary to the target polynucleotide sequence to form a double stranded nucleic acid product cleaving the redox moiety from the double stranded nucleic acid product; and electrochemically detecting a signal from the cleaved redox moiety, wherein a detectable signal is indicative of the presence of the second amplified polynucleotide product.

In some embodiments, the nuclease is capable of cleaving the oligonucleotide probe at the modified internal residue when hybridized to a complementary target nucleic acid sequence. In some instances, the nuclease is not capable of cleaving the oligonucleotide probe unless hybridized to a complementary nucleic acid sequence.

In some embodiments, the process of amplifying the first and second amplified polynucleotide product comprises Recombinase Polymerase amplification (RPA) or nicking and extension amplification reaction (NEAR). In some instances, electrochemically detecting a signal is performed using differential pulse voltammetry, amperometry, or impedance measurement.

In some embodiments, prior to cleavage of the oligonucleotide probe by the nuclease, the redox label does not generate an electrical current in response to the electrical potential applied across electrodes in contact with the nucleic acid amplification mixture.

In some embodiments of all aspects, the redox moiety is selected from the group consisting of a phenothiazine, a phenoxazine, a ferrocene, ruthenium (II), osmium (II), an anthraquinone, a phenazine, and derivatives thereof. In some embodiments, the redox moiety is a phenothiazine derivative selected from methylene blue or PZ9.

In some embodiments, the modified internal residue conjugated to a redox moiety has a structure selected from the group consisting of:

Formula I

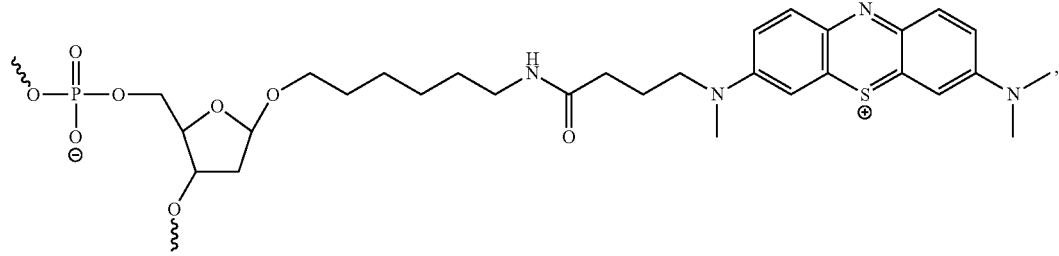

Methylene Blue

Formula II

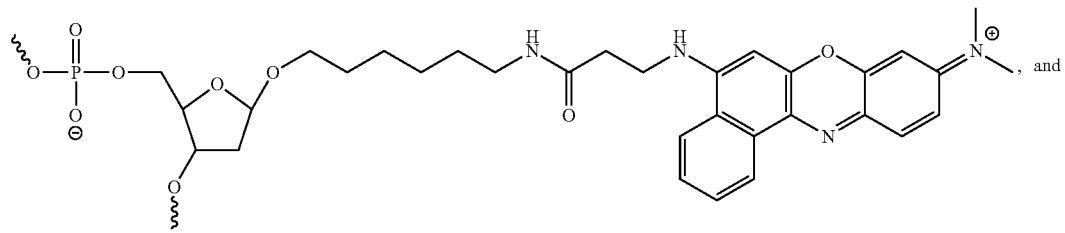

Nile Blue

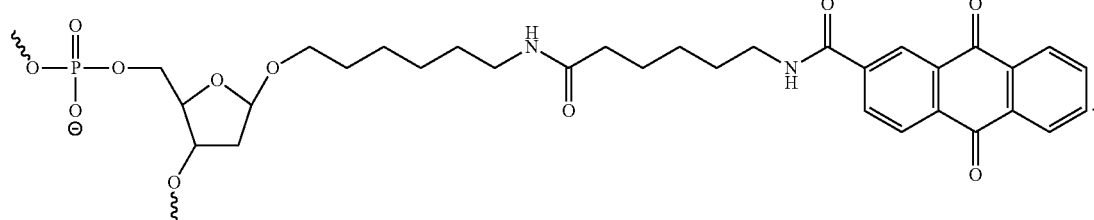

Anthraquinone-2-amidopentyl carboxylic acid
('AQ(C6)')

In some instances, wherein the modified internal residue conjugated to a redox moiety has a structure of:

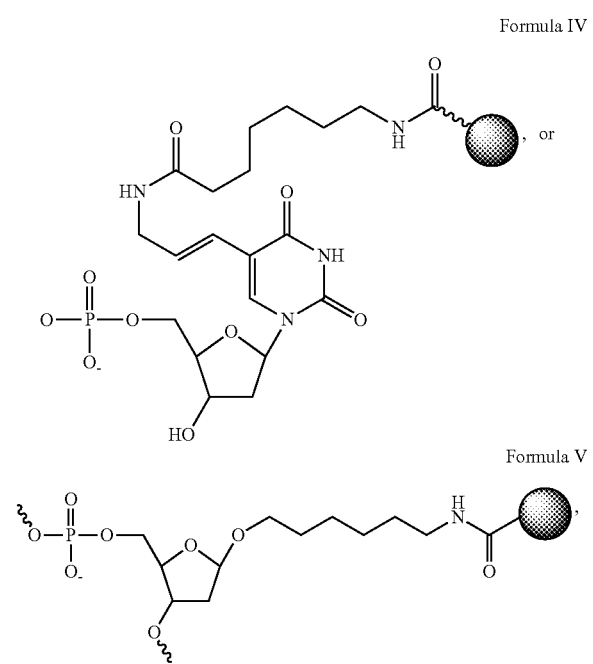

wherein

represents a redox moiety.

In some embodiments, the oligonucleotide can comprise more than one modified residues, e.g, two or more, three or more, or four or more modified residues, wherein each modified residue is conjugated to a redox moiety. For example, in some embodiments the oligonucleotide probe can comprise a first modified residue conjugated to a first redox moiety at a first internal site and a second modified residue conjugated to a second redox moiety at a second internal site. The first redox moiety and the second redox moiety can be the same, or different.

In some embodiments, the oligonucleotide probe is cleavable by a nuclease, e.g., AP endonuclease, DNA glycosylase/lyase or DNA glycosylase, at the non-complementary or modified residue when hybridized to a complementary nucleic acid sequence.

As used herein, the term "one or more" includes at least one, more suitably, one, two, three, four, five, ten, twenty, fifty, etc., of the item to which "one or more" refers.

The terms "first", "second", "third" and the like are used in this disclosure in their relative sense only. It will be understood that, unless otherwise noted, those terms are used merely as a matter of convenience in the description of one or more of the embodiments. The terms "first", "second", "third" and the like are only used to distinguish one element from another element, and the scope of the rights of the disclosed technology should not be limited by these terms. For example, a first element may be designated as a second element, and similarly the second element may be designated as the first element.

A "sample" as used herein refers to a biological material that is isolated from its environment (e.g., blood or tissue from an animal, cells, or conditioned media from tissue culture) and is suspected of containing, or known to contain an analyte or other desired material. A sample can also be a partially purified fraction of a tissue or bodily fluid, e.g., from a subject having a specific disease or condition. A sample can also be a crude sample or a sample that has not been purified. A sample can be diluted, treated with a lysing solution, or treated with an enzyme prior to use in the methods described herein. A reference sample can be a "normal" sample, from a donor not having the disease or condition. A reference sample can also be from an untreated donor or cell culture not treated with an active agent (e.g., no treatment or administration of vehicle only) or not subjected to conditions to induce a disease state. A reference sample can also be taken at a "zero time point" prior to contacting the cell with the agent to be tested.

As used herein, the term "patient" or "subject" is used throughout the specification to describe an animal, human or non-human, rodent or non-rodent, to whom treatment according to the methods of the present invention is provided. Veterinary and non-veterinary applications are contemplated. The term includes but is not limited to birds, reptiles, amphibians, and mammals, e.g., humans, monkeys and other primates, pigs, rodents such as mice and rats, rabbits, guinea pigs, hamsters, cows, horses, cats, dogs, sheep and goats. Preferred subjects are humans (adult, juvenile, or neonate), farm animals, and domestic pets such as cats and dogs.

The terms "nucleic acid", "polynucleotide" and "oligonucleotide" refer to primers, probes, oligomer fragments to be detected, oligomer controls and unlabeled blocking oligomers and shall be generic to polydeoxyribonucleotides (containing 2-deoxy-D-ribose), to polyribonucleotides (containing D-ribose), and to any other type of polynucleotide which is an N glycoside of a purine or pyrimidine base, or modified purine or pyrimidine bases. There is no intended distinction in length between the term "nucleic acid", "polynucleotide" and "oligonucleotide", and these terms will be used interchangeably. These terms refer only to the primary structure of the molecule. Thus, these terms include double- and single-stranded DNA, as well as double- and single stranded RNA.

As used herein, the term "oligonucleotide" refers to a nucleic acid comprised of a sequence of approximately at least 6 nucleotides, preferably at least about 10-12 nucleotides, and more preferably at least about 15-20 nucleotides corresponding to a region of the designated nucleotide sequence. "Corresponding" means identical to or complementary to the designated sequence.

As used herein and in the claims, the term "target nucleic acid", "target sequence" or "target nucleic acid sequence" refers to a region of the nucleic acid which is to be either amplified, detected or both. The target sequence resides between the two primer sequences used for amplification.

The term "probe" or "oligonucleotide probe" are used interchangeably and refer to a labeled oligonucleotide which forms a duplex structure with a sequence in the target nucleic acid, due to complementarity of at least one sequence in the probe with a sequence in the target region. In some embodiments, the probes are attached onto a solid surface (e.g., an electrode surface).

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

FIGS. 1A-1B depict an embodiment of an electrochemical detection method according to the present disclosure.

FIG. 2 depict a DPV trace illustrating the detection of methylene blue (MB) on a HeartCheck sensor during an RPA reaction. The MB peak sits within the ideal potential window for detecting cleaved labels, falling as it does between the strongly sloping baseline at $\lesssim -0.5$ mV, and a background peak which rises at $\gtrsim -0.28$ V.

DETAILED DESCRIPTION

Figure 3A:
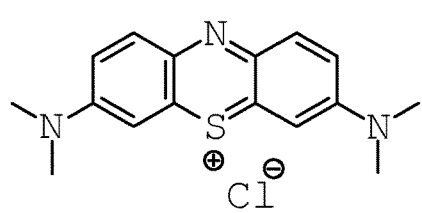
FIGS. 3A-3C depict the (3A) structural formula of methylene blue (MB); (3B) structural formula of MB NHS-ester, Biosearch product #MB-1000S-5; and the (3C) generalized method of labelling RPA probes with MB and other redox labels.

Oligonucleotide probes, compositions comprising the oligonucleotide probes, and method of use thereof for monitoring (i.e., detecting, quantifying) a target nucleic acid sequence are disclosed. In particular, the present disclosure provides novel oligonucleotide probes (e.g., redox labeled oligonucleotides) and associated methods for electrochemical detection of amplified polynucleotide products. The principal underlying this electrochemical (or 'Echem') detection method is depicted in FIG. 1.

The disclosure provides oligonucleotide probes labeled with one or more electrochemically active labels, including, for example a redox moiety. The term "label" as used herein and in the claims refers to any atom or molecule which can be used to provide a detectable signal, including a quantifiable signal, and which can be attached to a nucleic acid or protein. Labeled oligonucleotide probes provided herein are capable of producing a unique and detectable electrochemical signal following release of the redox moiety from hybridization of the oligonucleotide probe to a target nucleic acid sequence and sequence-dependent cleaving (i.e., release) of the redox moiety from the oligonucleotide. Where the redox moiety has been cleaved from the oligonucleotide probes (i.e., a sample positive for the target nucleic acid) a peak in current is observed at a voltage which corresponds to the oxidation potential of the label.

As used herein, a 'redox moiety' or 'redox label' refers to any atom or molecule that may be detected using a reduction potential for electrochemical read-out. A non-limiting list of redox moieties suitable for use in the oligonucleotides disclosed herein include, for example, ferricyanide, ferrocene, nicotinamide adenine dinucleotide (phosphate), diamines, phenanthroline, ruthenium (II), osmium (II), anthraquinone, quinone, phenothiazine, phenazine, phenoxazine, dichlorophenolindophenol tetrazolium dyes, phenylimino-benzophenoxazine, and derivatives thereof. Additional examples of redox moieties suitable for use in the oligonucleotides disclosed herein can be found, for example, in EP1481083, EP1808494 and U.S. Pat. No. 6,134,461, all of which are incorporated herein by reference. The variety of moieties that may be coupled to the residue suggest multiple strategies to detect successful processing of the probe as evidence of the presence of a specific target nucleic acid.

A non-limiting list of phenothiazine derivatives suitable for use as redox moieties in the compositions and methods disclosed herein are provided in Table 1.

TABLE 1

| Designation | Chemical Name and Structure† |
|---|---|
| Methylene Blue | 3,7-bis(Dimethylamino)-phenothiazin-5-ium chloride |
| PZ1 | Mono(triethylammonium) 5-(3-phenothiazinylideneamino)isophthalate |
| PZ2 | 5-(2-Methoxy-3-phenothiazinylideneamino)isophthalic acid |

TABLE 1-continued

| Designation | Chemical Name and Structure† |
|---|---|
| PZ3 | 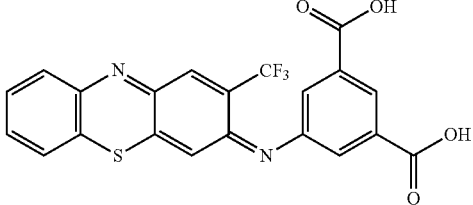 [SMILES: O=C(O)c1cc(/N=c2/cc3sc4ccccc4nc-3cc2C(F)(F)F)cc(C(=O)O)c1]<br>5-(trifluoromethyl-3-phenothiazinylideneamino)isophthalic acid |
| PZ4 | 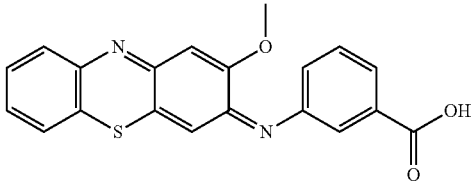 [SMILES: COc1cc2nc3ccccc3sc-2c/c1=N/c1cccc(C(=O)O)c1]<br>m-(2-Methoxy-3-phenothiazinylideneamino)benzoic acid |
| PZ5 | 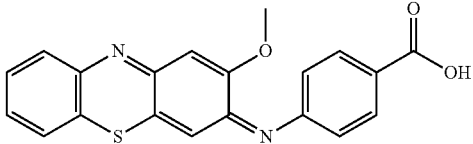 [SMILES: COc1cc2nc3ccccc3sc-2c/c1=N/c1ccc(C(=O)O)cc1]<br>p-(2-Methoxy-3-phenothiazinylideneamino)benzoic acid |
| PZ6‡ | 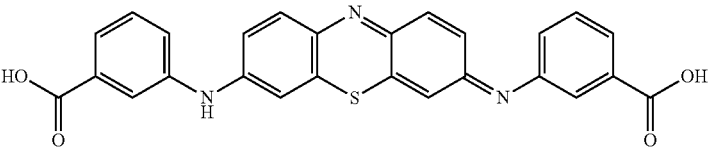 [SMILES: O=C(O)c1cccc(/N=c2\ccc3nc4ccc(Nc5cccc(C(=O)O)c5)cc4sc-3c2)c1]<br>m-(7-(m-Carboxyphenylamino)-3-phenothiazinylideneamino)benzoic acid |
| PZ7 | 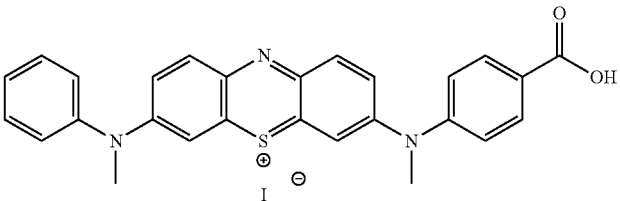<br>3-(N-Methyl-N-(p-carboxyphenyl)amino)-7-(N-methyl-N-phenylamino)-phenothiazin-5-ium iodide |
| PZ8 | 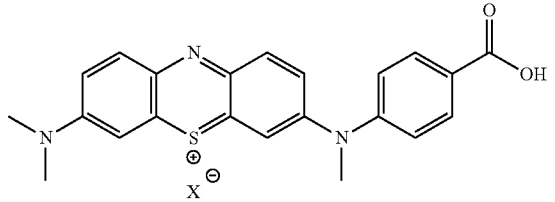<br>3-(N,N-Dimethylamino)-7-(N-methyl-N-(p-carboxyphenyl)amino)-phenothiazin-5-ium chloride/iodide |

TABLE 1-continued

| Designation | Chemical Name and Structure† |
|---|---|
| PZ9 | 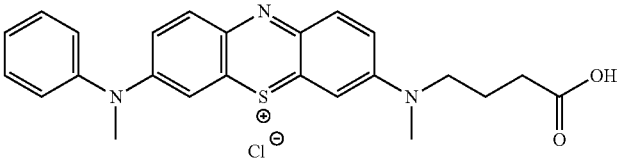 [SMILES: CN(CCCC(=O)O)c1ccc2nc3ccc(N(C)c4ccccc4)cc3[s+]c2c1 ; [Cl-]]<br>3-(N-Methyl-3-carboxypropyl)amino)-7-(N-methyl-N-phenylamino)-phenothiazin-5-ium chloride |
| PZ10* | 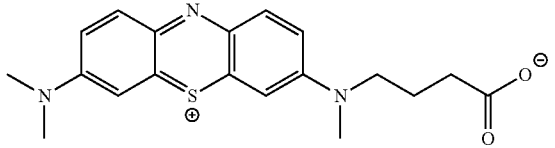 [SMILES: CN(C)c1ccc2nc3ccc(N(C)CCCC(=O)[O-])cc3[s+]c2c1]<br>4-(N-Methyl(7-dimethylamino)-3-phenothiazin-5-iumyl)amino)butyrate |
| PZ11 | 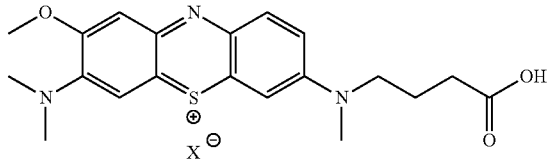<br>3-(N,N-Dimethylamino)-2-methoxy-7-(N-methyl-N-(3-carboxypropyl)amino)phenothiazin-5-ium chloride/iodide |
| Methylene green (zinc chloride double salt) | 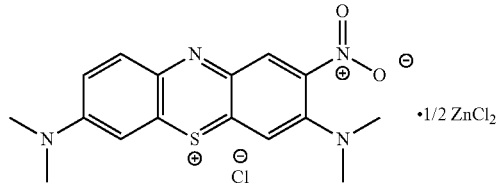 [SMILES: CN(C)c1ccc2nc3cc([N+](=O)[O-])c(N(C)C)cc3[s+]c2c1 ; [Cl-]] |
| Toluidine Blue O | 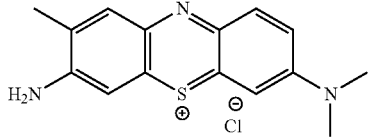 [SMILES: Cc1cc2nc3ccc(N(C)C)cc3[s+]c2cc1N ; [Cl-]] |
| Azure A | 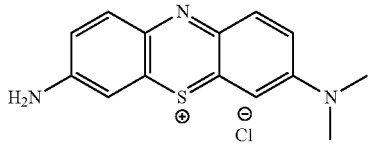 [SMILES: CN(C)c1ccc2nc3ccc(N)cc3[s+]c2c1 ; [Cl-]] |
| 1,9-Dimethyl-Methylene Blue (zinc chloride double salt) | 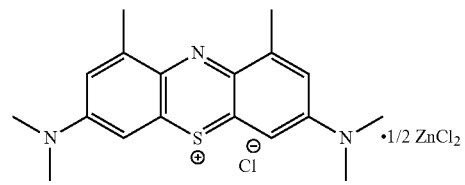 |

Phenoxazines represent a distinct class of redox-active organic compounds that bear a structural similarity to the phenothiazines described above. A non-limiting list of phenoxazines derivatives suitable for use as redox moieties in the compositions and methods disclosed herein are provided in Table 2.

TABLE 2

| Designation | Chemical Name and Structure† |
|---|---|
| PO1 | 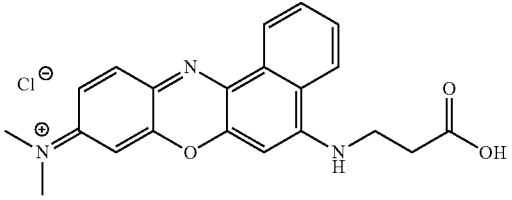 [SMILES: C[N+](C)=c1ccc2nc3c(cc(NCCC(=O)O)c4ccccc43)oc-2c1 ; [Cl-]]<br>N-(5-(2-carboxyethylamino)-9H-benzo[a]phenoxazin-9-ylidene)-N-methylmethanaminium chloride |
| PO2 | 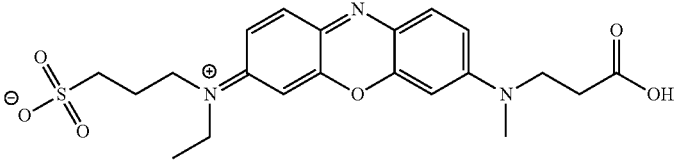 [SMILES: CC/[N+](CCCS(=O)(=O)[O-])=c1/ccc2nc3ccc(N(C)CCC(=O)O)cc3oc-2c1]<br>N-(3-(N-methyl(2-carboxyethyl)amino)phenoxazin-7-ylidene)-N-ethyl(3-sulfonatopropyl)aminium chloride |
| PO3 | 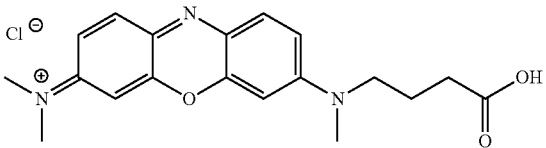 [SMILES: CN(CCCC(=O)O)c1ccc2nc3ccc(=[N+](C)C)cc-3oc2c1 ; [Cl-]]<br>N-(3-(N-methyl(3-carboxypropyl)amino)phenoxazin-7-ylidene)-N-methylmethanaminium chloride |
| PO1 derivative | 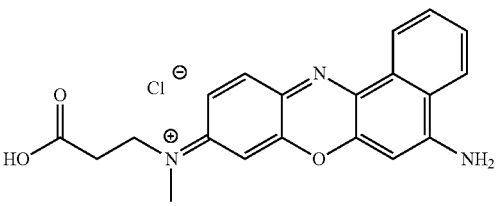 [SMILES: C/[N+](CCC(=O)O)=c1/ccc2nc3c(cc(N)c4ccccc43)oc-2c1 ; [Cl-]] |
| gallocyanine | 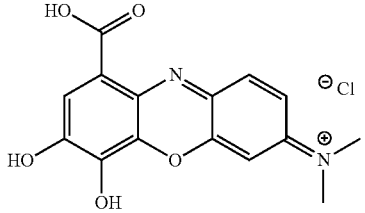 [SMILES: C[N+](C)=c1ccc2nc3c(C(=O)O)cc(O)c(O)c3oc-2c1 ; [Cl-]] |
| Meldola's blue | 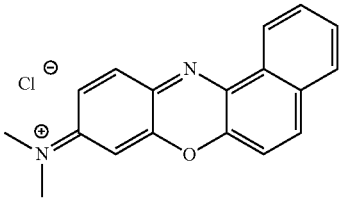 [SMILES: C[N+](C)=c1ccc2nc3c(ccc4ccccc43)oc-2c1 ; [Cl-]] |
| Nile Blue | 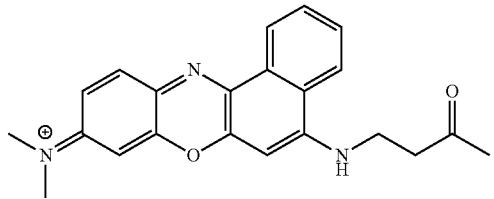 [SMILES: CC(=O)CCNc1cc2oc3cc(=[N+](C)C)ccc-3nc2c2ccccc12] |

Phenazines represent a distinct class of redox-active organic compounds that bear a structural resemblance to the phenothiazines and phenoxazines described above. A non-limiting example of a phenazine suitable for use as a redox moiety in the compositions and methods is provided below (Formula VI):

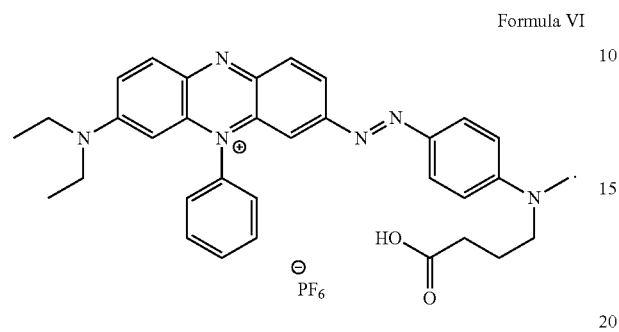

Formula VI

A further class of redox-active organic compounds suitable for use as redox moieties in the compositions and methods are anthraquinones and derivatives thereof. A non-limiting list of anthraquinone derivatives suitable for use as redox moieties in the compositions and methods disclosed herein are provided in Table 3.

TABLE 3

| Name | Chemical Structure |
| --- | --- |
| 9,10-anthraquinone | 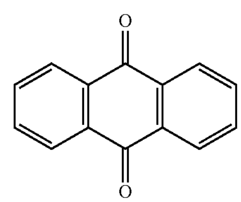 [SMILES: O=C1c2ccccc2C(=O)c2ccccc21] |
| 9,10-anthraquinone-2-carboxylic acid | 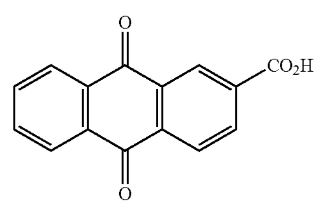 [SMILES: O=C(O)c1ccc2c(c1)C(=O)c1ccccc1C2=O] |
| 9,10-anthraquinone-2,3-dicarboxylic acid | 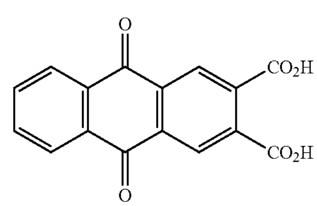 [SMILES: O=C(O)c1cc2c(cc1C(=O)O)C(=O)c1ccccc1C2=O] |
| 1-nitro-9,10-anthraquinone-2-carboxylic acid | 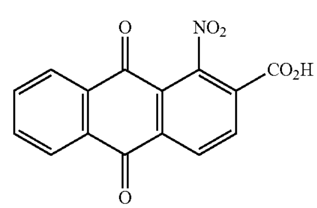 [SMILES: O=C1c2ccccc2C(=O)c2c1ccc(C(=O)O)c2[N+](=O)[O-]] |

TABLE 3-continued
| Name | Chemical Structure |
|---|---|
| 2-methylaminocarbonyl-9,10-anthraquinone | 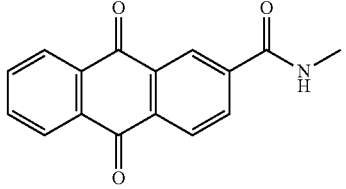 [SMILES: CNC(=O)c1ccc2c(c1)C(=O)c1ccccc1C2=O] |
| 14-Methyl-14-azatetracyclo[8.7.0.03,8.012,16]heptadeca-1(10),3(8),4,6,11,16-hexaene-2,9,13,15-tetrone | 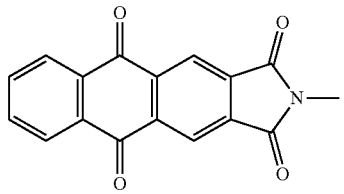 [SMILES: Cn1c(=O)c2cc3c(=O)c4ccccc4c(=O)c3cc2c1=O] |
| 5,8-disulfo-9,10-anthraquinone-2-carboxylic acid | 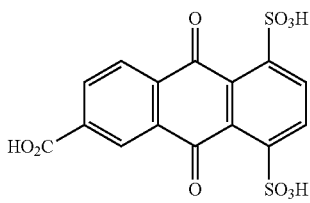 [SMILES: O=C(O)c1ccc2c(c1)C(=O)c1c(S(=O)(=O)O)ccc(S(=O)(=O)O)c1C2=O] |
| 5,8-dinitro-9,10-anthraquinone-2-carboxylic acid | 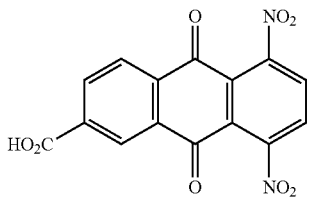 [SMILES: O=C(O)c1ccc2c(c1)C(=O)c1c([N+](=O)[O-])ccc([N+](=O)[O-])c1C2=O] |
| 6,7-dinitro-9,10-anthraquinone-2-carboxylic acid | 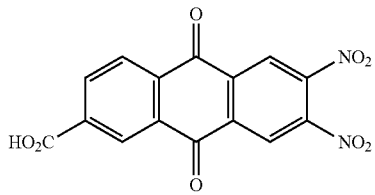 [SMILES: O=C(O)c1ccc2c(c1)C(=O)c1cc([N+](=O)[O-])c([N+](=O)[O-])cc1C2=O] |
| N-(6-carboxy-9,10-anthraquinon-2-yl)-N,N,N-trimethylammonium chloride | 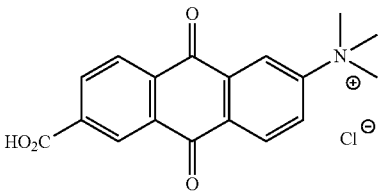 [SMILES: C[N+](C)(C)c1ccc2c(c1)C(=O)c1ccc(C(=O)O)cc1C2=O ; [Cl-]] |
| 6-sulfo-9,10-anthraquinone-2-carboxylic acid | 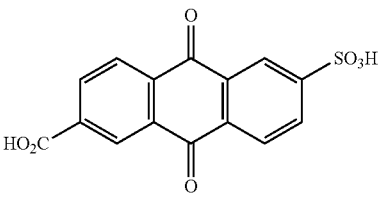 [SMILES: O=C(O)c1ccc2c(c1)C(=O)c1ccc(S(=O)(=O)O)cc1C2=O] |

TABLE 3-continued
| Name | Chemical Structure |
|---|---|
| 9,10-anthraquinone-2,6-disulfonic acid | 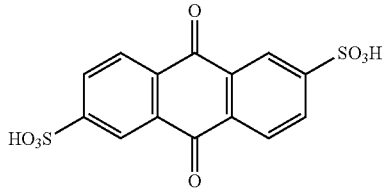 [SMILES: O=C1c2ccc(S(=O)(=O)O)cc2C(=O)c2ccc(S(=O)(=O)O)cc21] |
| 7-sulfo-9,10-anthraquinone-2-carboxylic acid | 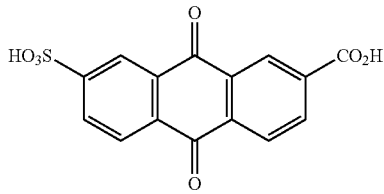 [SMILES: O=C(O)c1ccc2c(c1)C(=O)c1cc(S(=O)(=O)O)ccc1C2=O] |
| 9,10-anthraquinone-2-sulfonic acid | 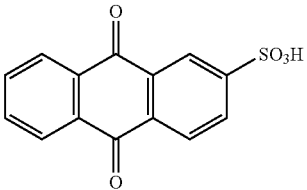 [SMILES: O=C1c2ccccc2C(=O)c2cc(S(=O)(=O)O)ccc21] |
| 9,10-anthraquinone-2-amidopentyl carboxylic acid | 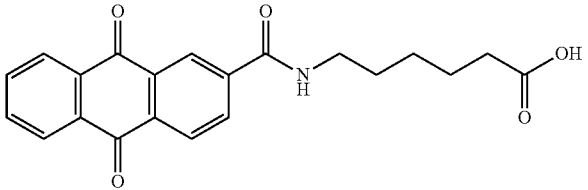 [SMILES: O=C(O)CCCCCNC(=O)c1ccc2c(c1)C(=O)c1ccccc1C2=O] |
| 5-sulfo-9,10-anthraquinone-2-carboxylic acid | 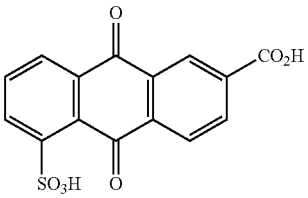 [SMILES: O=C(O)c1ccc2c(c1)C(=O)c1cccc(S(=O)(=O)O)c1C2=O] |
| 8-sulfo-9,10-anthraquinone-2-carboxylic acid | 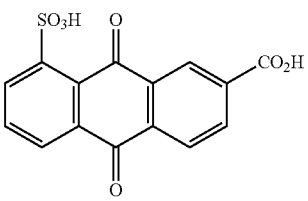 [SMILES: O=C(O)c1ccc2c(c1)C(=O)c1c(cccc1S(=O)(=O)O)C2=O] |
| 9,10-anthraquinone-2,7-disulfonic acid | 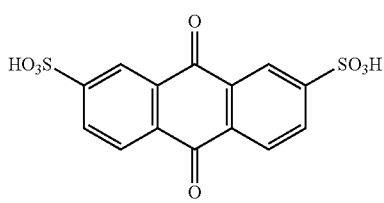 |

TABLE 3-continued

| Name | Chemical Structure |
| --- | --- |
| 9,10-anthraquinone-1-sulfonic acid | 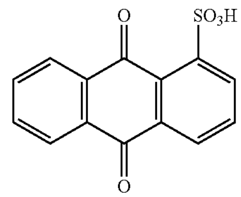 [SMILES: O=C1c2ccccc2C(=O)c2c1cccc2S(=O)(=O)O] |

'Metal complexes', which are defined by the identity of the metal and its associated ligands, are exemplary redox moieties suitable for use in the oligonucleotide probes disclosed herein.

Ruthenium (II) complexes are provided as a further class of redox moieties suitable for use as redox moieties in the compositions and methods for electrochemical (Echem) detection described herein. The commercially available NHS ester of a Ru(II) complex is provided (Formula II, Sigma-Aldrich product #96631):

Formula VII

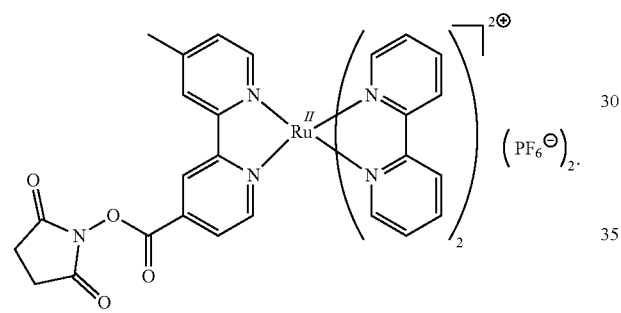

Osmium (II) complexes are provided as a further class of redox moieties suitable for use as redox moieties in the compositions and methods for Echem detection described herein. Chemical structure of the octahedral Os(II) complex synthesized in-house, [Os(bpy)2(cbpy)](PF6)$_2$ is provided (Formula III):

Formula VIII

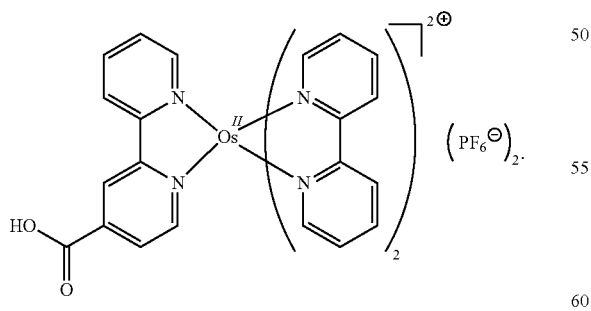

Iron (II) complexes are provided as a further class of redox moieties in the compositions and methods for Echem detection described herein. Chemical structures of exemplary carboxylic acid-functionalized ferrocene derivatives for RPA probe labelling are provided below (Formula IX and X):

Formula IX

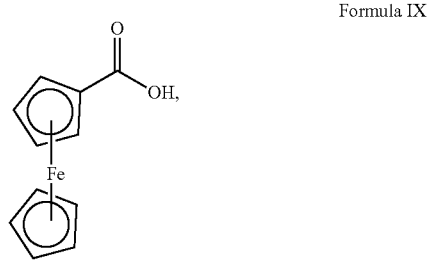

Formula X

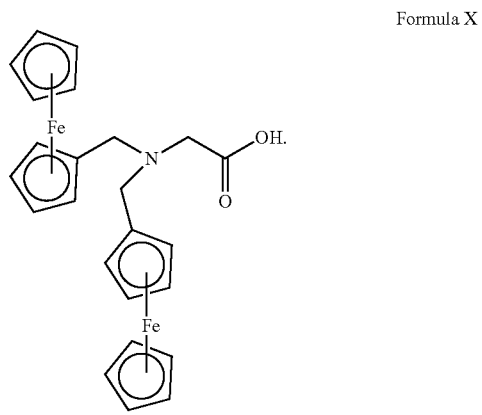

In some embodiments, the redox moiety is conjugated to the oligonucleotide probe. For example, the redox moiety can be conjugated to an internal non-complementary or modified residue. Exemplary redox-moieties modified for conjugation to an oligonucleotide probe of the present disclosure are described herein and shown below:

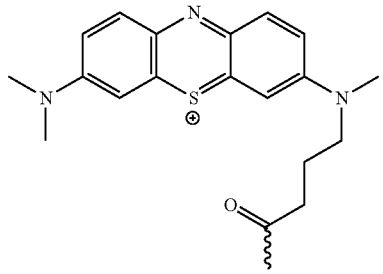

MB = Methylene Blue

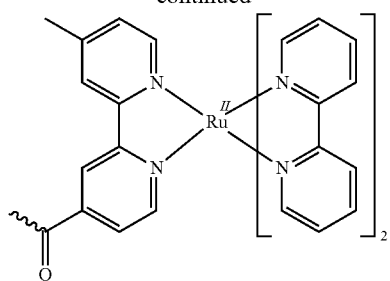

Ru(II) = [Ru(bpy)₂(mcbpy)]²⁺

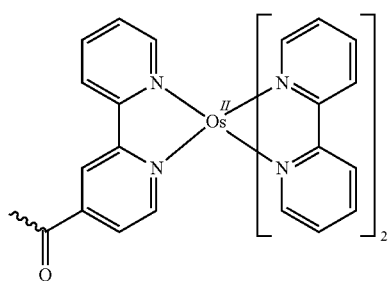

Os(II) = [Os(bpy)₂(cbpy)]²⁺

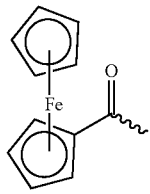

Fc = Ferrocene

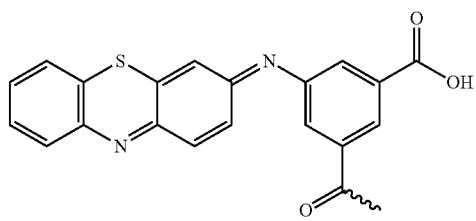

CP1 = 5-((3H-Phenothiazin-3-ylidene)amino)isophthalic acid

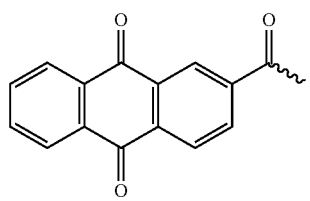

AQ = anthraquinone-2-carboxylic acid

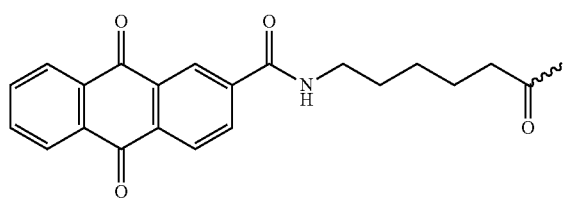

AQ(C6) = anthraquinone-2-amidopentyl carboxylic acid

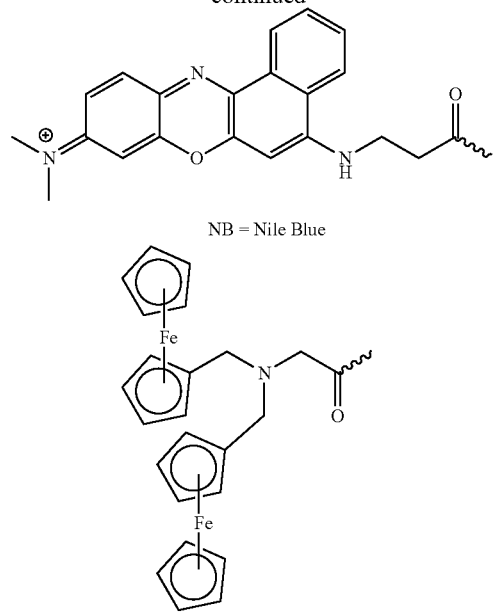

NB = Nile Blue

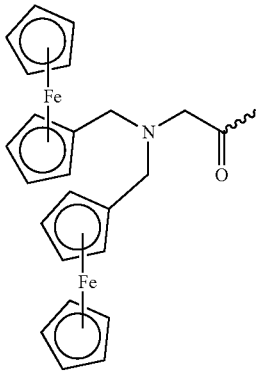

Di-Fc = di-ferrocene, or
N,N-(diferrocenylmethyl)glycine

Figure 12:
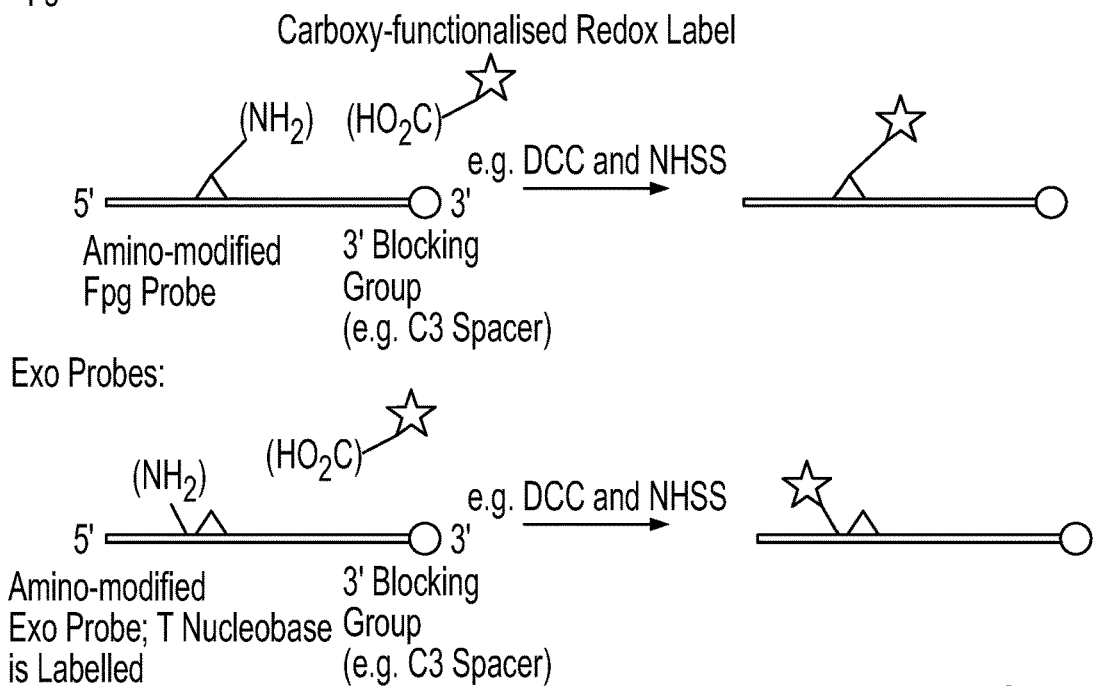
FIG. 12 depicts an exemplary conjugation process for preparing an Exo and a Fpg oligonucleotide probe labeled with redox-moieties of the present disclosure.

The redox moiety can be conjugated an oligonucleotide via synthesis of labelled phosphoramidite during automated DNA synthesis or through the post-synthetic labeling of oligonucleotides, which can allow for alternative attachment chemistries when a phosphoramidite is not available for a particular label. For example, a 'click' reaction (Cu-catalyzed or Cu-free SPAAC) could be used to attach an azide-functionalized label/oligo to an alkyne-functionalized oligo/label. Alternatively, an active ester derived from a carboxy-functionalized label/oligo can be reacted with an amino-functionalized oligo/label (see FIG. 12).

Attachment of a redox label at a position 5' of a THF ('d spacer') residue of an Exo RPA probe oligonucleotide will allow release of the redox label upon digestion of the probe by the Exo enzyme. As in normal RPA, the Exo enzyme will only cleave the THF residue in the presence of the complementary RPA-derived amplicon. 3'-to-5' digestion of the 5' fragment of the resulting oligo by Exo will then release the redox label appended to a nucleotide fragment. The redox label is now electrochemically detectable because it is attached to this smaller nucleotide fragment, as opposed to an oligonucleotide.

Figure 13:
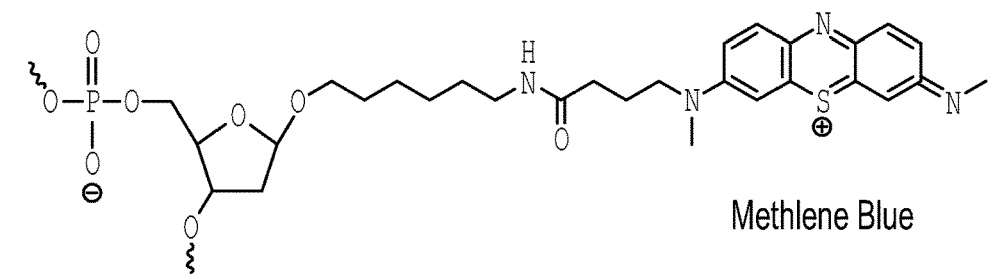
FIG. 13 depicts the structures of exemplary Fpg modifications. The chemical structures of the modified residues containing redox-labeled Fpg cleavage positions are shown with methylene blue, Nile Blue, and anthraquinone-2-amidopentyl carboxylic acid ('AQ(C6)').
Figure 13:
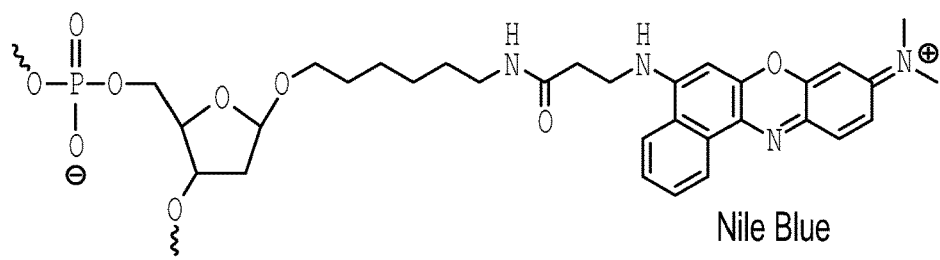
Figure 13:
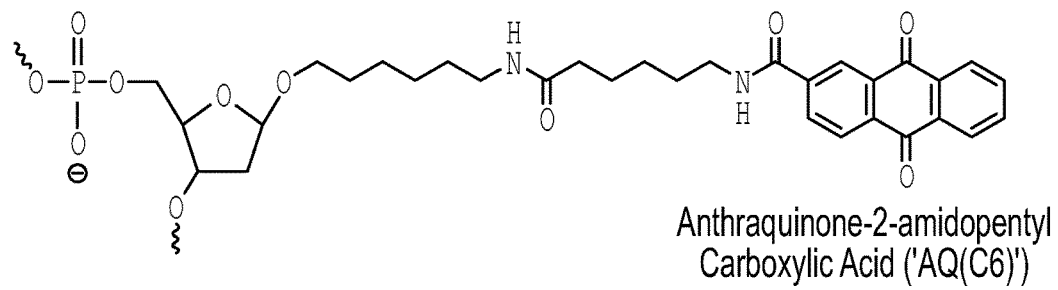

As a non-limiting example, methylene blue-labelled Fpg probes are readily prepared by reacting amino-dR-functionalized oligonucleotides (externally sourced from e.g. Eurogentec S. A., Belgium) with methylene blue NHS ester (externally sourced from e.g. Biosearch Technologies, Inc., USA); the resulting probes are purified by RP-HPLC and desalted before use. It is also feasible that methylene blue-labelled Fpg probes can be prepared directly by standard solid phase synthesis techniques on automated synthesizers, through the use of the appropriate methylene blue-functionalized phosphoramidite. Exemplary structures of Fpg modifications are shown in FIG. 13.

Figure 14:
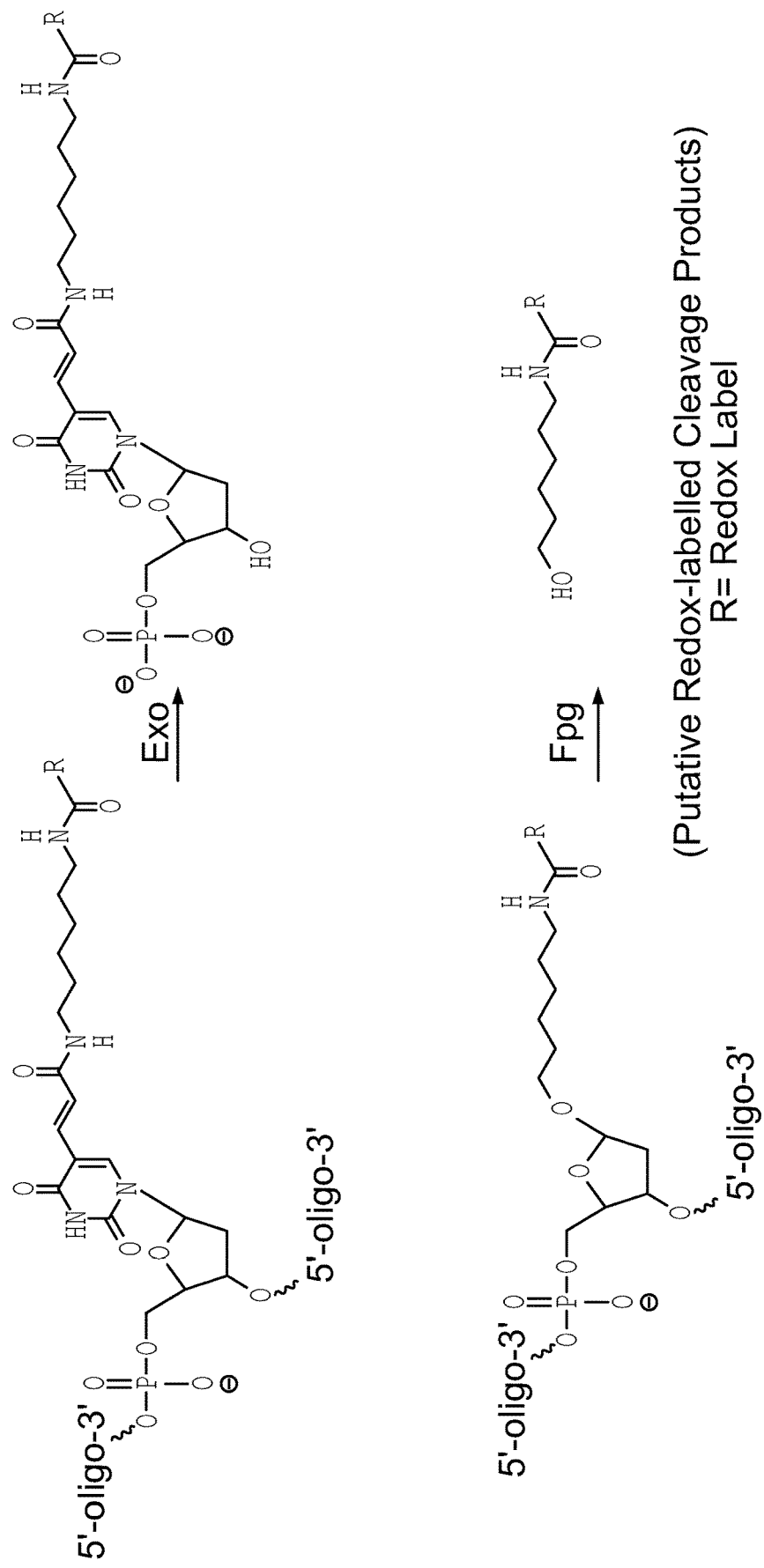
FIG. 14 depicts cleavage of oligonucleotide probes and release of redox-moieties as provided in the present disclosure.

Putative products following cleavage of the oligonucleotides probes of the present disclosure using Exo and Fpg are shown in FIG. 14.

Further, any of the processes of this disclosure may be performed with a blocked primer. A blocked primer is a primer which does not allow elongation with a polymerase. Thus, in some embodiments, the oligonucleotide probes disclosed herein comprise a 3' blocking group. This 3' group prevents polymerase extension of the oligonucleotide. Where a blocked primer is used, an unblocking agent can be used to unblock the primer to allow elongation. The unblocking agent may be an endonuclease or exonuclease which can cleave the blocking group from the primer. Exemplary unblocking agents include ExoIII, Nfo, and *E. coli* endonuclease IV.

In some embodiments, the electrochemically active label is conjugated to the oligonucleotide probe at an internal non-complementary (i.e., non-complementary to a target nucleic acid sequence) or modified residue. Thus, in some embodiments, the oligonucleotide probe comprises an internal non-complementary or modified residue. Non-limiting examples of an internal non-complementary or modified residue include an abasic residue, tetrahydrofuran (d-spacer), and a dR-O—[C]n nucleotide that lacks a base and has a sugar with a carbon at a 1' position, and wherein the carbon at the 1' position is covalently linked through an oxygen atom to a carbon atom of a linker containing n carbon atoms, in which the linker is conjugated to the redox moiety; or uracil, as described in WO2010/135310, which is incorporated herein in its entirety.

In some embodiments of the oligonucleotide probe, the probe comprises more than one modified residues and more than one redox moieties. For example, the oligonucleotide probe can comprise a first modified residue conjugated to a first redox moiety at a first internal site and a second modified residue conjugated to a second redox moiety at a second internal site. The more than one redox moieties can be the same or can be different. In some embodiments the oligonucleotide probe can comprise a $3^{rd}$, $4^{th}$, $5^{th}$, or $6^{th}$ modified residue conjugated to a $3^{rd}$, $4^{th}$, $5^{th}$ or $6^{th}$ redox moiety respectively at a $3^{rd}$, $4^{th}$, $5^{th}$, or $6^{th}$ internal site respectively.

The oligonucleotide probes, as described herein, can be complementary to a target gene sequence. In some embodiments the oligonucleotide probes are complementary to a target human gene sequence. In some embodiments the oligonucleotide probes are complementary to a target non-human gene sequence, e.g., a bacterial, viral, parasitic, or fungal gene sequence. In some embodiments the target gene sequence is complementary to a *Streptococcus pyogenes* gene sequence, an Influenza A gene sequence, or an Influenza B gene sequence. Examples of such sequences are described herein. In some embodiments, the target gene sequence is complementary to a gene sequence of a bacteria, including, for example a bacteria of the genus *Acetobacter, Acinetoacter, Actinomyces, Agrobacterium, Anaplasma, Azorhizobium, Azotobacter, Bacillus, Bacteroides, Baronella, Bordetella, Borrelia, Brucella, Burkholderia, Calymmatobacterium, Campylobacter, Chlamydia, Chlamydophila, Clostridium, Corynebacterium, Coxiella, Ehrlichia, Enterobacter, Enterococcus, Escherichia, Francisella, Fusobacterium, Gardnerella, Haemophilus, Helicobacer, Klebsiella, Lactobacillus, Legionella, Listeria, Methanobacterium, Microbacterium, Micrococcus, Moraxella, Mycobacterium, Mycoplasma, Neisseria, Pasteurella, Peptostreptococcus, Porphyromonas, Prevotella, Pseudomonas, Rhizobium, Rickettsia, Rochalimaea, Rothia, Salmonella, Shigella, Spirillum, Staphylococcus, Stenotrophomonas, Streptococcus, Treponema, Vibrio, Wolbachia,* and/or *Yersinia*. In some embodiments, the target gene sequence is complementary to a *Campylobacter* gene sequence, a *Salmonella* gene sequence, or a *Listeria* gene sequence. In some embodiments, the target gene sequence is complementary to a gene sequence of a virus, including, for example a virus of the family Adenoviridae, Herpesviridae, Papillomaviridae, Polyomaviridae, Poxviridae, Hepadnaviridae, Parvoviridae, Astroviridae, Caliciviridae, Picornaviridae, Coronaviridae, Flaviviridae, Togaviridae, Hepeviridae, Retroviridae, Orthomyxoviridae, Arenaviridae, Bunyaviridae, Filoviridae, Paramyxoviridae, Rhabdoviridae, and/or Reoviridae. In some embodiments, the target gene sequence is complementary to a gene sequence of a fungus, including, for example a fungus of the genus *Aspergillus, Blastomyces, Candida, Coccidioides, Cryptococcus* (e.g., *C. neoformans* and *C. gattii*), *Histoplasma, Pneumocystis, Stachybotrys, Sporothrix, Exserohilum,* and/or *Cladosporium*. In some embodiments, the target gene sequence is complementary to a parasite gene sequence, including, for example, an *Acanthocephala,* an *Ascariasis* (roundworms), a *Cestoda* (tapeworms, e.g., *Taenia saginata* (human beef tapeworm), *Taenia solium* (human pork tapeworm), *Diphyllobothrium latum* (fish tapeworm) or *Echinococcosis* (hydatid tapeworm)), a *Clonorchis sinensis* (the Chinese liver fluke), a *Dracunculus medinensis* (Guinea worm), an *Enterobius vermicularis* (pinworm), a *Filariasis*, a Hookworm, a *Loa loa*, an *Onchocerciasis* (river blindness), a *Schistosomiasis*, a *Strongyloides stercoralis*, a *Toxocara canis* (dog roundworm), a *Trichinella*, a Whipworm, a Ring worm, an *Entamoeba histolytica*, an *Entamoeba coli*, an *Acanthamoeba*, a *Balamuthia mandrillaris*, a *Giardia*, a *Cyclospora cayetanensis*, a *Cryptosporidium*, a *Toxoplasma gondii*, a *Leishmania* (e.g., *L. tropica, L. donovani,* and L. *Mexicana*), a *Plasmodium* (e.g, *P. falciparum, P. vivax,* and *P. malariae*), or a *Babesia* gene sequence.

The embodiments described herein can also include an agent capable of cleaving a target nucleic acid sequence in a sequence dependent manner. For example, an agent capable of cleaving the oligonucleotide probe described herein at the non-complementary or modified residue when hybridized to a complementary nucleic acid sequence.

As used herein, the term "nuclease" refers to enzymes capable of catalyzing the hydrolysis of nucleic acids, cleaving the phosphodiester bonds between the nucleotide subunits of nucleic acids. A "restriction nuclease" is a nuclease that targets and cleaves a nucleic acid molecule at or near specific recognition nucleotide sequences known as restriction sites. Nucleases may be further divided into endonucleases (i.e., enzymes that cleave the phosphodiester bond within a polynucleotide chain) and exonucleases (i.e., enzymes that work by cleaving nucleotides one at a time from the end (exo) of a polynucleotide chain), although some of the enzymes may fall in both categories. The nuclease can be a naturally occurring restriction endonuclease or an artificial endonuclease.

Throughout the disclosure, the terms "restriction enzyme" and "restriction endonuclease" are used interchangeably and refer to a nuclease that targets and cleaves a double stranded nucleic acid at or near a restriction site, cutting of both strands of the target nucleic acid to yield a blunt ended or sticky ended cut site. Different restriction endonucleases recognize different recognition sequences, are known to persons skilled in the art, and are available from various commercial sources.

In some embodiments of all aspects, the agent capable of cleaving double stranded nucleic acid at a target cleavage sequence is a "restriction endonuclease." Through the use of the restriction endonuclease, a specific nucleotide sequence is targeted as determined by the specific restriction site, resulting in cleavage of both strands to yield a blunt ended or sticky ended fragment. The resulting fragment having a blunt or sticky end prevents further replication of both strands between the regions of nucleic acid that are complementary to the forward and reverse primers. As a result, there is no replication of the complimentary strand and thus no exponential increase in the number of copies of the nucleic acid to which the probe will bind.

In some embodiments of all aspects, the agent capable of cleaving double stranded nucleic acid at a target cleavage sequence is a DNA glycosylase or a glycosylase/lyases (for example an abasic (AP) lyase). DNA glycosylase or a glycosylase/lyases are a family of enzymes involved in base excision repair, by which damaged bases in DNA are removed and replaced. DNA glycosylase or a glycosylase/lyases suitable for use in the methods disclosed herein include, for example, ExoIII, Fpg, Nfo, Nth, MutY, MutS, MutM, E. coli MUG, human MUG, human Ogg1, a vertebrate Nei-like (Neil) glycosylase, uracil glycosylase, or hypoxanthine-DNA.

Examples of the restriction endonucleases described herein include AatII, AbaSI, Acc65I, AccI, AciI, AclI, AcuI, AfeI, MTH, AflIII, AgeI, AhdI, AleI, AluI, AlwI, AlwNI, ApaI, ApeKI, ApoI, BamHI, BanI, BbvI, BccI, BcgI, BglII, BglII, BmgBI, BmrI, BpmI, BsaAI, BsaBI, BsaHI, BsaI, BsgI, BsII, BsmAI, CspCI, ClaI, Cac8I, DdeI, DpnI, DrdI, EaeI, EagI, EarI, EcoRI, FatI, FseI, HaeII, HhaI, HindIII, I-CeuI, KasI, KpnI, LpnPI, MboI, MboII, MfeI, MluCI, MlyI, MmeI, MseI, MsII, MspI, NaeI, NarI, NdeI, HheI, NlaIII, NotI, PacI, PaeR7I, PciI, PhoI, PleI, PmeI, PshAI, PspGI, PstI, PvuI, RsaI, SacI, SacII, SalI, SapI, SbfI, ScaI, SexAI, SfaNI, SfoI, SmlI, SpeI, StuI, StyD4I, Tfil, TseI, Tsp45I, Tth111I, XbaI, XcmI, XhoI, XmaI, ZraI, and any functional analogs or homologs thereof. One of skill in the art would appreciate that any restriction endonuclease could be used, including for example, an artificial restriction enzyme (i.e., an artificial nuclease).

The compositions described herein can further comprise one or more nucleic acid primers. In some embodiments of any of the aspects described here, nucleic acid primers consist, comprise, or consist essentially of an oligonucleotide having a length of at least or about 10 nucleotides, at least about 20 nucleotides, at least about 30 nucleotides, at least about 40 nucleotides, or at least 50 nucleotides.

The compositions described herein can be provided in a kit. The kit can also include combinations of the compositions described herein. The kit can include (a) an oligonucleotide probe as described herein, (b) a nuclease, (c) informational material, and/or any combination of (a)-(c). For example, the kits can include an oligonucleotide as described herein and a nuclease, wherein the nuclease is capable of cleaving the oligonucleotide probe at the non-complementary or modified residue when hybridized to a complementary nucleic acid sequence. In some embodiments the kit can include a nuclease wherein the nuclease is not capable of cleaving the oligonucleotide probe unless hybridized to a complementary nucleic acid sequence; i.e. the nuclease only cleaves the oligonucleotide probe when it is hybridized to a complementary nucleic acid sequence. In some embodiments the kit can include a nuclease, wherein the nuclease is an AP endonuclease, DNA glycosylase/lyase (for example a DNA glycosylase/AP lyase) and/or a DNA glycosylase. In some embodiments the nuclease is Fpg or ExoIII.

Figure 15:
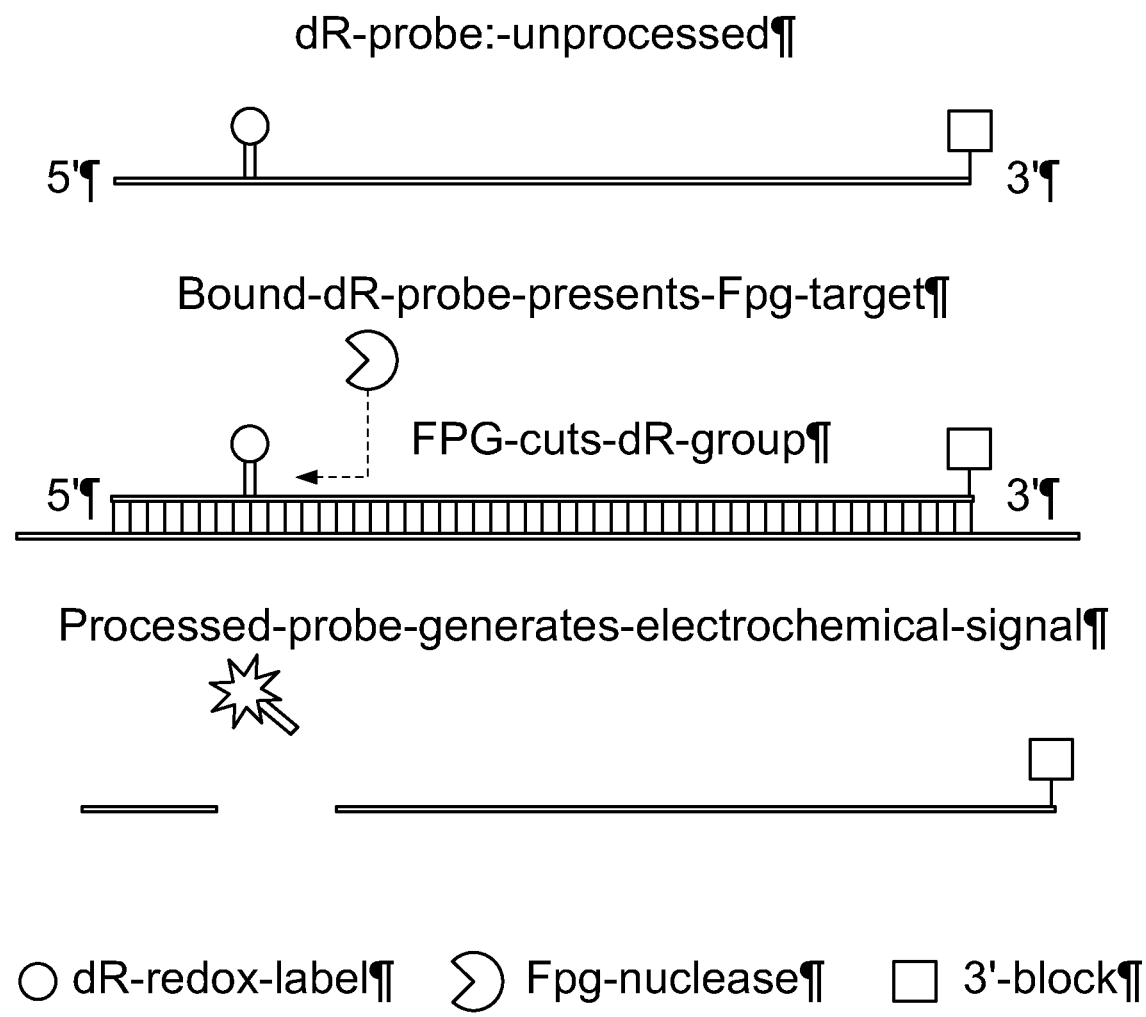
FIG. 15 depicts an oligonucleotide probe design as provided in the present disclosure. Demonstrating an example of a probe design, including an oligonucleotide body, an internal dR-redox-label nucleotide analogue and a 3' polymerase extension block. Upon alignment with a complementary sequence, the Fpg cleaves at the redox-labeled Fpg cleavage site releasing the redox-label for electrochemical detection. Without alignment of the complementary sequences, cleavage by Fpg and release of the redox-label does not occur, resulting in the absence of electrochemical signal.

Referring to FIG. 15, an oligonucleotide probe containing an internal residue conjugated to a redox moiety at an Fpg cleavage site can be cut by Fpg. Exemplary oligonucleotide probes containing internal residues conjugated to methylene blue as the redox-moiety for electrochemical detection are provided below.

The sequence of an exemplary probe ("FluAPAdRP5 echem") is below: 5' ACCCAXGGATCATTAATCAGG-CACTCCTCAATTGCTT (Spacer C3) 3', wherein X=redox-labelled Fpg cleavage position (SEQ ID NO: 8). The exemplary probe ("FluAPAdRP5 echem") oligonucleotide probe contains a dR-methylene blue modified internal residue susceptible to Nfo and/or fpg cleavage, and is blocked on the 3' by virtue of a 2',3'dideoxycytidine residue (Spacer C3). Methylene blue (MB) has a reduction peak potential of −320 mV vs Ag/AgCl during DPV in an RPA context.

Additional non-limiting examples of redox-labeled probes for electrochemical detection of RPA follow:

InfA[PA]:
(SEQ ID NO: 1)
5'AAGCAATTGAGGAGTGCCTGATTAAT[dR-methylene blue]ATCCCTGGGTTTTG 3';

InfA[PB2]:
(SEQ ID NO: 2)
5'GTCTGGCTGTCAGTAAGTAT[dR-methylene blue]CTAGAGTCCCGTTTT 3';

InfB[PA]:
(SEQ ID NO: 3)
5'TCAGCTACAATCAAGACTACTCGTTAA[dR-methylene blue]TAATGAATCCTCAT 3';

Control (IC):
(SEQ ID NO: 4)
5'GCACACTTGTCACCTACATTTCTGATT[dR-methylene blue]GTGGACTCTAACAT 3';

(SEQ ID NO: 5)
5' CATCAGCTTTTGGAGCTTGAGAGTCAT[T(methylene blue)]A[dSpacer]GTTTTTGAGCTTCAC 3';

(SEQ ID NO: 6)
5' GAACCAAGAAGCATTRAGCAAAACCCAGGGA[T(methylene blue)][dSpacer]ATTAATCAGGCACTC 3';

(SEQ ID NO: 7)
5' ACTGATGATATTCAGC[T(methylene blue)]ACAA[T(methylene blue)]CAAGAC[T(methylene blue)]A[dSpacer]TCGTTAAGTAATGAA 3';

(SEQ ID NO: 9)
5' AATACCGCGAGGTG[dR-methylene blue]AGCAAATCTAT[dR-methylene blue]AAATATGTCCCAGT;

(SEQ ID NO: 10)
5' ATTTTCTCTGGATG[dR-methylene blue]TATGCCCGGTAAAC AGATGA[dR-methylene blue]TATTGATGCCGATT;
and (SEQ ID NO: 11)
5' TCGAAAAGAAACAC[dR-methylene blue]CGGATGAAATCGAT AAGT[dR-methylene blue]TATACAAGGATTGG.

A range of alternative redox labels were investigated and may also be used, including, for example, ferrocene, ruthenium (II), osmium (II), anthraquinone, phenazine, phenothiazine and phenoxazine derivatives as useful signaling molecules for RPA. The phenothiazine derivative, designated 'PZ9', was found to generate a DPV current response comparable to that for MB and at a potential differentiated from both background and MB peaks. Two phenoxazine derivatives (Nile Blue and EVOblue™ 30) were also discovered to provide a DPV current response comparable to that for MB.

In another aspect, this disclosure features methods of determining the presence or absence of a target nucleic acid in a sample that include: (a) contacting the target nucleic acid sequence with a mixture including: a first primer and a second primer for amplifying the target nucleic acid sequence; a recombinase, a polymerase, an oligonucleotide probe comprising one or more internal non-complementary or modified residues conjugated to a redox moiety and a 3' blocking group to prevent polymerase extension, and an agent capable of cleaving double-stranded nucleic acid at a target cleavage sequence; (b) performing a nucleic acid amplification reaction of the mixture for production of nucleic amplification products in the mixture; and (c) electrochemically monitoring the rate of increase of nucleic acid amplification products in the mixture, due to release of label from probe that has formed double stranded structures with complementary sequence.

DNA and RNA amplification by RPA can be monitored in real-time or by end-product detection using the TwistAmp® basic kit with DPV detection. Briefly, a clinical sample (e.g., a clinical swab or wipe) is added to an RPA reagent mixture specific for a target nucleic acid sequence, the reagent mixture containing an Exo or Fpg oligonucleotide probe labeled with a redox-moiety, such as those described above, and maintained at 37° C.-42° C. for a time sufficient for amplification. Incubation in the presence of an ExoIII or Fpg exonuclease results in cleavage of probe/target DNA hybrids which allows for liberation of the redox-moiety (see FIG. 14). The liberated redox-moiety can be detected by, for example, amperometry, voltammetry (e.g., Differential Pulse voltammetry), and AC-impedance. Where the redox label has been cleaved from the probe/target complex (i.e., a sample positive for the target nucleic acid) a peak in current is observed at a voltage which corresponds to the oxidation potential of the label. Where the redox label has not been released from the oligonucleotide probe (i.e., a sample negative for the target nucleic acid), no peak is observed.

A "DPV output" of a given RPA reaction is determined by measuring the signal current generated by the redox-label present in the reaction in response to applied potentials. The DPV procedure requires the definition of several key parameters: interval period (related to scan rate), step potential, amplitude of the pulse (amp) and time of the pulse (pulse width). An example of these settings were: interval period 0.1 s, step potential 5 mV, pulse amplitude 75 mV and pulse width 30 ms. In addition to these parameters for the actual measurement, the DPV protocol also entails a series of 3 initial sequences of potential changes ("sweeps") the output of which is not being directly quantified. These pre-measurement sweeps have been shown to increase the signal amplitude of the 4th measurement sweep, possibly by altering the interaction of redox-label and electrode surface ("preconditioning").

In some embodiments the methods described herein disclose a method of identifying the presence or absence of a target nucleic acid sequence in a sample. The method can include the steps of (a) contacting a sample with the compositions described herein, (b) contacting the mixture with a nuclease, (c) maintaining the mixture under conditions that allow for production of nucleic acid amplification products, (d) contacting the mixture with a nuclease, and (e) detecting an electrical signal generated by the redox label. The composition of (a) can include at least one recombinase, at least one polymerase, a single stranded DNA binding protein, at least one agent that is capable of cleaving DNA between defined bases, and an oligonucleotide probe comprising one or more internal non-complementary or modified residue conjugated to a redox moiety and a 3' blocking group to prevent polymerase extension to form a mixture. The detection of an electrical signal identifies the presence of the target nucleic acid sequence. When the target nucleic acid sequence is absent, the oligonucleotide probe will not hybridize with the complementary nucleic acid sequence and the nuclease will not cleave the oligonucleotide. In some embodiments if the redox label is not released/cleaved from the oligonucleotide, an electrical signal will not be identified.

In some methods described herein, the nuclease is capable of cleaving the oligonucleotide probe at the non-complementary or modified residue when hybridized to a complementary nucleic acid sequence. In some methods, the nuclease is not capable of cleaving the oligonucleotide probe unless hybridized to a complementary nucleic acid sequence. In some methods, prior to cleavage of the oligonucleotide probe by the nuclease, the redox label does not generate an electrical current in response to the electrical potential applied across electrodes in contact with the reaction mixture.

In some embodiments the electrical signal detected can be an electrical current. Thus, this disclosure provides methods for electrochemically monitoring of nucleic acid amplification reactions. The electrochemical methods allow for direct sensing of synthesized amplicons associated with one or more electrochemically active labels as described herein. Electrochemical signal amplification can be detected according to methods known to the skilled artisan including, for example, amperometry, voltammetry (e.g., Differential Pulse voltammetry), and AC-impedance. The electrical current can be detected by known techniques, e.g., differential pulse voltammetry, amperometry, or impedance measurement.

In the methods described herein, the oligonucleotide probe contains an internal non-complementary or modified residue; e.g. an uracil, an abasic residue, tetrahydrofuran (d-spacer), and/or a dR-O—[C]n nucleotide that lacks a base and has a sugar with a carbon at a 1' position, and wherein the carbon at the 1' position is covalently linked through an oxygen atom to a carbon atom of a linker containing n carbon atoms, in which the linker is conjugated to the redox moiety. The redox moiety described in the methods herein can be selected from a phenothiazine, a phenoxazine, a ferrocene, ruthenium (II), osmium (II), an anthraquinone, a phenazine, and derivatives thereof; e.g., a phenothiazine derivative such as methylene blue and PZ9; a phenoxazine derivative such as Nile blue or EVOblue™ 30; Ru(II); Os(II); Fc; CP1, AQ; AQ(C6); and/or Di-Fc. The modified residue conjugated to the redox moiety can have a structure as described herein, e.g. in Formula I, II and/or III.

In another embodiment described herein, the method comprises (a) contacting an oligonucleotide probe comprising one or more internal non-complementary or modified residue conjugated to a redox moiety and a 3' blocking group to prevent polymerase extension with a target nucleic acid, in order to form an oligonucleotide-nucleic acid complex in a reaction mixture; (b) contacting the oligonucleotide-nucleic acid complex in the reaction mixture with a nuclease; and (c) detecting an electrical signal generated by an electrical signal generated by the redox label in response to an electrical potential applied across electrodes in contact with the reaction mixture. In some embodiments the electrical signal is an electrical current and can be detected via known methods; e.g. differential pulse voltammetry, amperometry, or impedance measurement. In some embodiments, if the oligonucleotide probe is not cleaved then the redox label does not generate an electrical current in response to the electrical potential applied across electrodes in contact with the reaction mixture. In some embodiments prior to cleaving the oligonucleotide probe, the redox label does not generate an electrical current in response to the electrical potential applied across electrodes in contact with the reaction mixture.

In some embodiments the nuclease will not cleave the oligonucleotide probe unless it is hybridized to a complementary nucleic acid sequence (e.g., the target nucleic acid sequence). In some embodiments the nuclease will cleave the oligonucleotide probe if is it hybridized to a complementary nucleic acid sequence (e.g., the target nucleic acid sequence). As described, the nuclease of the methods described herein can be selected from the group consisting of AP endonuclease, DNA glycosylase/lyase and DNA glycosylase.

In the methods described herein, the oligonucleotide probe can comprise the non-complementary or modified residues described herein or any combination thereof. In the methods described herein, the redox moiety can be selected from the redox labeled described or any combination thereof (e.g., a phenothiazine, a phenoxazine, a ferrocene, ferrocene derivatives, ruthenium (II), osmium (II), an anthraquinone, a phenazine, and derivatives thereof). Further in some embodiments of the methods described herein, the oligonucleotide comprises more than one modified residue conjugated to a redox moiety at an internal site, as described herein. This capacity to multiply the redox-label provides for the ability to increase the electric signal.

The methods described herein provide for direct detection of amplified products associated with one or more electrochemically active labels as described herein. Thus, in some aspects, this disclosure provides methods for electrochemically monitoring of nucleic acid amplification reactions. Electrochemical detection of liberated redox moiety can be performed using methods and devices known to the skilled artisan including, methods known to the skilled artisan including, for example, amperometry, voltammetry (e.g., Differential Pulse voltammetry (DPV)), and AC-impedance.

The disclosure includes methods for amplifying a target nucleic acid comprising a target polynucleotide sequence to prepare an amplified polynucleotide product. Amplification of polynucleotides is a standard procedure for detecting small amounts of nucleic acid in life science research and molecular diagnostics. Nucleic acids (e.g., polynucleotides) suitable for amplification in connection with the present methods include double-stranded and single-stranded nucleic acid molecules, such as DNA and RNA molecules. The polynucleotides may be of genomic, chromosomal, plasmid, mitochondrial, cellular, and viral nucleic acid origin. For double stranded polynucleotides, the amplification may be of either one or both strands.

Amplification methods suitable for use in the present methods include amplification methods performed isothermally. For example, the amplification may be performed without subjecting the polynucleotides to thermal cycling, e.g., by maintaining a temperature of the polynucleotides to within +/−20° C., to within +/−C, to within +/−10° C., to within +/−5° C., to within +/−2.5° C., or at a substantially constant temperature during amplification.

Isothermal polynucleotide amplification technologies suitable for use in the present methods include recombinase polymerase amplification (RPA) as described in U.S. Pat. No. 7,399,590. Isothermal technologies for performing multiplexed amplification of polynucleotides include multiplexed recombinase polymerase amplification as described in U.S. Pat. No. 8,580,507 and multiplexed recombinase amplification as described in an article by Ming et al. (Integrated Quantum Dot Barcode Smartphone Optical Device for Wireless Multiplexed Diagnosis of Infected Patients, ACS Nano, 2015, 9 (3), pp 3060-3074). Each of the foregoing references is incorporated herein by reference in its entirety and considered part of the present disclosure.

As described here, RPA employs enzymes, known as recombinases, which are capable of pairing oligonucleotide primers with homologous sequences in template double-stranded nucleic acid. RPA introduces a recombinase for inserting two primers with a template in duplex DNA, a single stranded DNA-binding protein for stabilizing the displaced strands of DNA and for preventing the primers from being displaced, and strand-displacing polymerase for extending primers bound to template DNA. In this way, DNA synthesis is directed to defined points in a template double-stranded nucleic acid. Using two or more sequence-specific (e.g., gene-specific) primers, an exponential amplification reaction is initiated if the template nucleic acid is present. The reaction progresses rapidly and results in specific amplification of a sequence present within the template double-stranded nucleic acid from just a few copies of the template nucleic acid to detectable levels of the amplified products within minutes. Importantly, RPA process proceed under isothermal conditions under physiological temperature of 37-42° C. RPA methods are disclosed, e.g., in U.S. Pat. Nos. 7,270,981; 7,399,590; 7,666,598; 7,435,561; US 2009/0029421; and WO 2010/141940, all of which are incorporated herein by reference.

RPA depends upon components of the cellular DNA replication and repair machinery, and relies upon establishment of a 'dynamic' recombination environment having adequate rates of both recombinase loading and unloading that maintains high levels of recombination activity achieved in the presence of specific crowding agents. RPA has the advantage that it combines the sensitivity, specificity and most other features of PCR but without the need for thermocycling and with extraordinary speed and robustness to off-temperature set-up. RPA has already benefited from the potential employment of a wide variety of nucleic acid processing enzymes such as known repair endonucleases which have been untapped by other processes because of either the need for thermostable equivalents or because they demonstrate poor regulation without accessory proteins such as single-stranded DNA binding proteins, a natural component of RPA reactions.

Briefly, RPA comprises the following steps: first, a recombinase agent is contacted with a first and a second nucleic acid primer to form a first and a second nucleoprotein primer. Second, the first and second nucleoprotein primers are contacted to a double stranded target sequence to form a first double stranded structure at a first portion of said first strand and form a second double stranded structure at a second portion of said second strand so the 3' ends of said first nucleic acid primer and said second nucleic acid primer are oriented towards each other on a given template DNA molecule. Third, the 3' end of said first and second nucleoprotein primers are extended by DNA polymerases to generate first and second double stranded nucleic acids, and first and second displaced strands of nucleic acid. Finally, the second and third steps are repeated until a desired degree of amplification is reached.

This disclosure also provides for a method of nested RPAs. In a nested RPA, a first region of nucleic acid is amplified by RPA to form a first amplified region. Then a second region of nucleic acid that is completely within the first amplified region is amplified using RPA to form a second amplified region. This process may be repeated as often as necessary. For example, a third region of nucleic acid, which is completely within the second region, may be amplified from the second amplified region by RPA.

The composition disclosed herein can contain a set of primers that amplify the target nucleic acid sequence. The primers can comprise of sequences that are complementary to the target nucleic acid sequence or that differ from the target nucleic acid sequence at one or more positions. As described herein, the amplification product, of RPA with a primer that differs from the target nucleic acid sequence at one or more positions, can differ from the target sequence at the one or more positions. The amplification product of the RPA reaction described herein can comprise a target cleavage sequence.

The set of primers can amplify the target nucleic acid sequence or they can introduce a sequence that differs from the target nucleic acid sequence at one or more positions. This introduced sequence can consist of a target cleavage sequence. The first primer can be complementary to the target nucleic acid sequence. The second primer can comprise a first portion that is complementary to the target nucleic acid sequence and a second portion that is different from the target nucleic acid sequence at one or more positions. When the two primers amplify the nucleic acid sequence the second primer incorporates the one or more different positions into the amplified products. This amplified region is different from the target nucleic acid sequence at the one or more positions and can consist of the target cleavage sequence.

The RPA composition disclosed herein contains a recombinase, which may originate from prokaryotic, viral or eukaryotic origin. Exemplary recombinases include RecA and UvsX (e.g., a RecA protein or UvsX protein obtained from any species), and fragments or mutants thereof, and combinations thereof. The RecA and UvsX proteins can be obtained from any species. RecA and UvsX fragments or mutant proteins can also be produced using the available RecA and UvsS protein and nucleic acids sequences, and molecular biology techniques (see, e.g., the mutant forms of UvsX described in U.S. Pat. No. 8,071,308). Exemplary UvsX proteins include those derived from myoviridae phages, such as T4, T2, T6, Rb69, Aeh1, KVP40, *Acinetobacter* phage 133, *Aeromonas* phage 65, cyanophage P-SSM2, cyanophage PSSM4, cyanophage S-PM2, Rb14, Rb32, *Aeromonas* phage 25, *Vibrio* phage nt-1, phi-1, Rb16, Rb43, Phage 31, phage 44RR2.8t, Rb49, phage Rb3, and phage LZ2. Additional exemplary recombinase proteins include archaebacterial RADA and RADB proteins and eukaryotic (e.g., plant, mammal, and fungal) Rad51 proteins (e.g., RAD51, RAD51B, RAD51C, RAD51D, DMC1, XRCC2, XRCC3, and recA) (see, e.g., Lin et al., Proc. Natl. Acad. Sci. U.S.A. 103:10328-10333, 2006).

In any process of this disclosure, the recombinase (e.g., UvsX) may be a mutant or hybrid recombinase. In some embodiments, the mutant UvsX is an Rb69 UvsX that includes at least one mutation in the Rb69 UvsX amino acid sequence, wherein the mutation is selected from the group consisting of (a) an amino acid which is not histidine at position 64, a serine at position 64, the addition of one or more glutamic acid residues at the C-terminus, the addition of one or more aspartic acid residues at the C-terminus, and a combination thereof. In other embodiments, the mutant UvsX is a T6 UvsX having at least one mutation in the T6 UvsX amino acid sequence, wherein the mutation is selected from the group consisting of: (a) an amino acid which is not histidine at position 66; (b) a serine at position 66; (c) the addition of one or more glutamic acid residues at the C-terminus; (d) the addition of one or more aspartic acid residues at the C-terminus; and (e) a combination thereof. Where a hybrid recombinase protein is used, the hybrid protein may, for example, be an UvsX protein that includes at least one region that includes an amino acid sequence derived from a different UvsX species. The region may be, for example, the DNA-binding loop-2 region of UvsX.

The DNA polymerase disclosed herein may be a eukaryotic or prokaryotic polymerase. Examples of eukaryotic polymerases include pol-alpha, pol-beta, pol-delta, pol-epsilon, and mutants or fragments thereof, or combinations thereof. Examples of prokaryotic polymerase include *E. coli* DNA polymerase I (e.g., Klenow fragment), bacteriophage T4 gp43 DNA polymerase, *Bacillus stearothermophilus* polymerase I large fragment, Phi-29 DNA polymerase, T7 DNA polymerase, *Bacillus subtilis* Pol I, *Staphylococcus aureus* Pol I, *E. coli* DNA polymerase I, *E. coli* DNA polymerase II, *E. coli* DNA polymerase III, *E. coli* DNA polymerase IV, *E. coli* DNA polymerase V, and mutants or fragments thereof, or combinations thereof. In some embodiments, the DNA polymerase lacks 3'-5' exonuclease activity. In some embodiments, the DNA polymerase has strand-displacing properties, e.g., large fragments of prokaryotic polymerases of class pol I or pol V.

Additionally, one or more single-stranded DNA binding proteins can be used to stabilize nucleic acids during the various exchange reactions that are ongoing in the reaction. The one or more single-stranded DNA binding proteins can be derived or obtained from any species, e.g., from a prokaryotic, viral or eukaryotic species. Non-limiting exemplary single-stranded DNA binding proteins include *E. coli* SSB and those derived from myoviridae phages, such as T4, T2, T6, Rb69, Aeh1, KVP40, *Acinetobacter* phage 133, *Aeromonas* phage 65, cyanophage P-SSM2, cyanophage PSSM4, cyanophage S-PM2, Rb14, Rb32, *Aeromonas* phage 25, *Vibrio* phage nt-1, phi-1, Rb16, Rb43, Phage 31, phage 44RR2.8t, Rb49, phage Rb3, and phage LZ2. Additional examples of single-stranded DNA binding proteins include *A. denitrificans* Alide_2047, *Burkholderia thailandensis* BthaB_33951, *Prevotella pollens* HMPREF9144_0124, and eukaryotic single-stranded DNA binding protein replication protein A.

Any of the processes of this disclosure may be performed in the presence of a crowding agent. In some embodiments, the crowding agent may include one or more of polyethylene glycol, polyethylene oxide, polyvinyl alcohol, polystyrene, Ficoll, dextran, poly(vinylpyrrolidone) (PVP), Triton-X, and albumin. In some embodiments, the crowding agent has a molecular weight of less than 200,000 daltons. In some embodiments of any of the aspects described here, the composition comprises a crowding agent selected from the group consisting of polyethylene glycol (PEG)(e.g., PEG1450, PEG3000, PEG8000, PEG10000, PEG14000, PEG15000, PEG20000, PEG250000, PEG30000, PEG35000, PEG40000, PEG compound with molecular weight between 15,000 and 20,000 daltons, or combinations thereof), dextran, polyvinyl alcohol, polyvinyl pyrrolidone, Triton-X, and Ficoll. In some embodiments, the crowding agent is present in the reaction mixture at a concentration between 1 to 15% by weight or by volume of the reaction mixture, e.g., between any two concentration values selected from 1.0%, 1.5%, 2.0%, 2.5%, 3.0%, 3.5%, 4.0%, 4.5%, 5.0%, 5.5%, 6.0%, 6.5%, 7.0%, 7.5%, 8.0%, 8.5%, 9.0%, 9.5%, 10.0%, 10.5%, 11.0%, 11.5%, 12.0%, 12.5%, 13.0%, 13.5%, 14.0% 14.5% and 15.0%.

If a recombinase loading protein is used, the recombinase loading protein may be of prokaryotic, viral or eukaryotic origin. Exemplary recombinase loading proteins include *E. coli* RecO, *E. coli* RecR, UvsY, and mutants or fragments thereof, or combinations thereof. Exemplary UvsY proteins include those derived from myoviridae phages, such as T4, T2, T6, Rb69, Aeh1, KVP40, *Acinetobacter* phage 133, *Aeromonas* phage 65, cyanophage P-SSM2, cyanophage PSSM4, cyanophage S-PM2, Rb14, Rb32, *Aeromonas* phage 25, *Vibrio* phage nt-1, phi-1, Rb16, Rb43, Phage 31, phage 44RR2.8t, Rb49, phage Rb3, and phage LZ2. In any of the processes of this disclosure, the recombinase loading agent may be derived from a myoviridae phage. The myoviridae phage may be, for example, T4, T2, T6, Rb69, Aeh1, KVP40, *Acinetobacter* phage 133, *Aeromonas* phage 65, cyanophage P-SSM2, cyanophage PSSM4, cyanophage S-PM2, Rb14, Rb32, *Aeromonas* phage 25, *Vibrio* phage nt-1, phi-1, Rb16, Rb43, Phage 31, phage 44RR2.8t, Rb49, phage Rb3, or phage LZ2.

Isothermal polynucleotide amplification technologies suitable for use in the present methods include Nicking and Extension Amplification Reaction (NEAR) as described in United States patent application publication nos. 2009/0081670 and 2009/0017453, each of which is incorporated herein by reference in its entirety and considered part of the present disclosure.

Amplification methods suitable for use in the present methods include amplification methods performed without subjecting the polynucleotides to a temperature sufficient to denature double stranded polynucleotides during the amplification. For example, the amplification of the polynucleotides may be performed without subjecting the polynucleotides to a temperature in excess of about C, about 80° C., about 70° C., or about 60° C. during amplification. In embodiments, the amplification of the polynucleotides is performed without subjecting the polynucleotides to conditions sufficient to denature double stranded polynucleotides during the amplification. For example, the amplification may be performed without subjecting the polynucleotides to physical, chemical, or thermal conditions sufficient to denature double stranded polynucleotides during amplification.

Amplification methods suitable for use in the present methods include amplification methods performed without first subjecting the polynucleotides to a temperature sufficient to denature double stranded polynucleotides present in the sample. For example, the amplification of the polynucleotides may be performed without first subjecting the polynucleotides to a temperature in excess of about 90° C., about 80° C., about 70° C., about 60° C., or about 55° C. In some embodiments, the polynucleotides and/or amplicons thereof are detected without first subjecting the polynucleotides to such excess temperatures. In some embodiments, the amplification of the polynucleotides is performed without first subjecting the polynucleotides to conditions sufficient to denature double stranded polynucleotides present in the sample. For example, the amplification may be performed without first subjecting the polynucleotides to physical, chemical, or thermal conditions sufficient to denature double stranded polynucleotides present in the sample.

Amplification methods suitable for use in the present methods include amplification methods performed in a total time (T) beginning with a step of combining the polynucleotides with reagents sufficient to perform the amplification and ending when amplification has proceeded by an amount sufficient to permit the qualitative or quantitative determination of the polynucleotides or amplicons thereof. In any of such embodiments, the total time T may be about 45 minutes or less, about minutes or less, about 20 minutes or less, or about 15 minutes or less.

The amplification of the polynucleotides includes, for example, amplifying the polynucleotides by at least about $10^6$ fold, at least about $10^7$ fold, at least about $10^8$ fold, at least about $10^9$ fold, at least about $10^{10}$ fold, at least about $10^{11}$ fold, or at least about $10^{12}$ fold. Such amplification may be performed within the time T.

Amplification methods suitable for use in the present methods include "real time" or "quantitative" polynucleotide amplification methods known to the skilled artisan. Such methods detect the accumulation of polynucleotide amplification product after each amplification cycle in real time as the reaction progresses, allowing for the determination of amplification kinetics. Real time methods are quantitative because the time (e.g., number of cycles) to reach a specific threshold concentration of amplified products directly relates to the initial copy number of the target nucleotide. According to some embodiments, the amplification reaction is monitored by electrochemical detection using the oligonucleotide probes described herein.

At FIG. 1, a method for electrochemical detection of an amplified nucleic acid target sequence according to an embodiment of the present invention is show. FIG. 1 demonstrates that in the absence of the amplified target nucleotide product, a redox label remains attached to the oligonucleotide probe, which limits the diffusion of the label moiety and its interaction with an electrode (e.g, screen printed carbon ('SPC') electrode). In the presence of the target, multiple copies of the DNA strand complementary to the labeled oligonucleotide probe are generated using a nucleic acid amplification method, such as, for example, PCR, RPA (shown), or NEAR. Following amplification, the DNA strand complementary to the labeled oligonucleotide probe anneal (i.e., hybridize) with the probe and form a double-stranded substrate. In the presence of a nuclease, the redox moiety (i.e., redox label) is enzymatically cleaved from (e.g., separated from) from the double-stranded substrate effecting release of the redox label. Once cleaved, the redox moiety (i.e., redox label) is able to diffuse and interact with the electrode and detection of the redox moiety is achieved by, for example, DPV, whereby a potential window (E) is swept in a stepwise fashion, and the Faradaic current (I) associated with reduction of the label is recorded. Diffusing redox labels that have been enzymatically released from oligonucleotide probes generate a larger current response, thus enabling electrochemical detection of target amplification.

Voltammetric detection of label release from oligonucleotide probe has been achieved by monitoring the current generated during either the reduction of a label (as shown in FIG. 1) or its oxidation. The potential at which a given label is oxidized or reduced is characteristic of that label and its molecular structure. These characteristics of a given redox moiety allow for multiplexed Echem analyte detection; if the redox potentials of two or more redox moieties are sufficiently different and resolved in the amplification medium, then attachment of these redox moieties to separate oligonucleotide probes targeted to different amplified polynucleotide products will facilitate the multiplexed detection of those amplified polynucleotide products in the same amplification reaction.

Any redox moiety for read-out desirably possesses a redox potential that is well resolved from background peaks which may derive from the complex amplification medium (e.g., the complex RPA medium) or the electrodes themselves. For example, during initial studies on Alere Heart-Check electrodes, redox moieties with a reduction potential (versus a Ag/AgCl reference electrode) of between approximately −0.50 and −0.28 mV were considered optimal for multiplexing (FIG. 2). In order to resolve two redox moieties which fall within this window, a difference (ΔE) of approximately ≥50 mV in their peak potential is predicted to be sufficient. Thus, in the case of the HeartCheck electrode, there is a theoretical maximum multiplexing capacity of 5 labels within this window. Note however that alternative (electrode-dependent) windows for detection may be determined.

EXAMPLES

The invention is further described in the following examples, which do not limit the scope of the invention described in the claims.

The following examples describe methods for detection of amplified target nucleic acid sequences that incorporate use of the novel oligonucleotide probes comprising electrochemical labels (i.e., redox-moieties) described herein.

Example 1: Methylene Blue

Figure 3B:
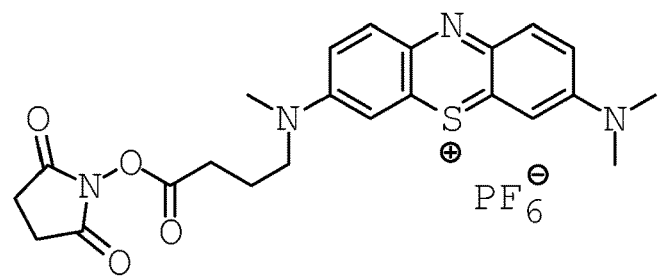
Figure 3C:
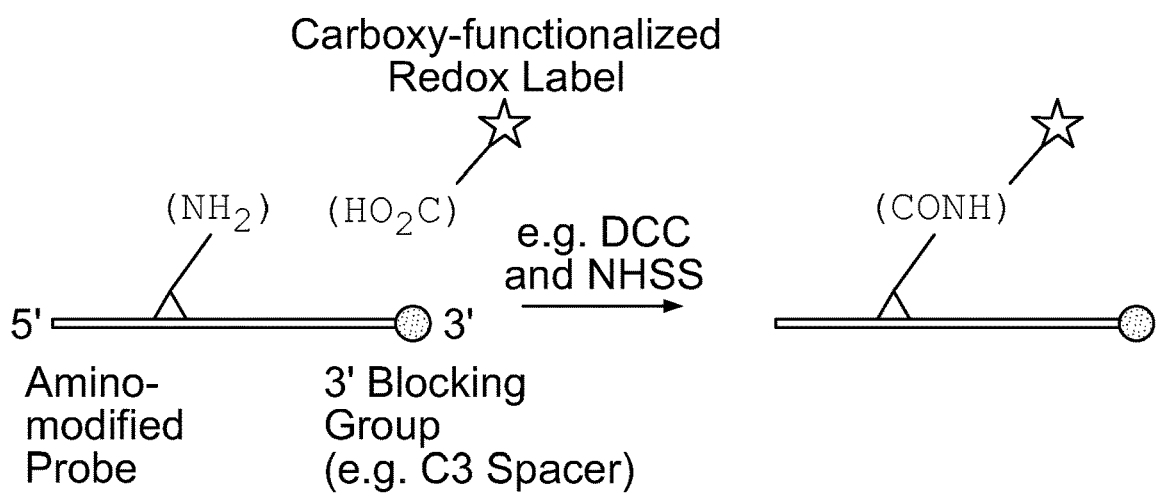

The electrochemical detection of RPA amplified polynucleotide products by enzymatic cleavage of redox-labelled oligonucleotide probes was demonstrated using methylene blue (MB), a cationic phenothiazine (or 'phenothiazinium') dye, as a label (FIG. 3).

The structure of MB may be modified with a carboxy-functionalized 'handle' to permit covalent attachment to amino-functionalized oligonucleotides. During oligonucleotide labelling, the carboxylic acid is activated, for example as an active ester by reaction with a carbodiimide (e.g. N,N'-dicyclohexylcarbodiimide, 'DCC') and N-hydroxysuccinimide ('NHS') in an organic solvent (e.g. N,N-dimethylformamide, 'DMF') before it is conjugated with an amino-modified oligo (see FIG. 3 (c)); this method of site-specifically functionalizing oligonucleotides has been extended to the derivatization of RPA probes with a variety of carboxy-functionalized labels, as described herein. The active NHS-ester of carboxy-functionalized MB is commercially available (e.g. from Biosearch Technologies, Inc., USA, product #MB-1000S-5; see FIG. 3 (b)). Multiple-labeled oligonucleotide probes are also contemplated.

Figure 4A:
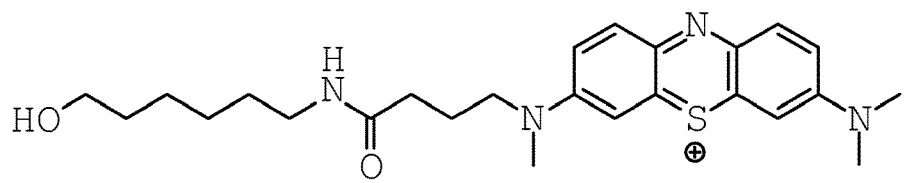
FIGS. 4A-4B depict the (4A) structural formula of an exemplary MB-labelled Fpg cleavage product; and the (4B) structural formula of an exemplary MB-labelled Exo cleavage product.
Figure 4B:
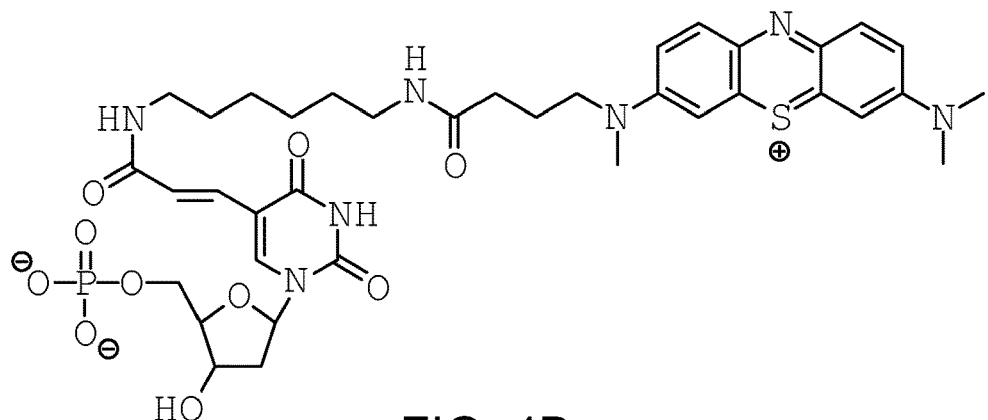
Figure 5A:
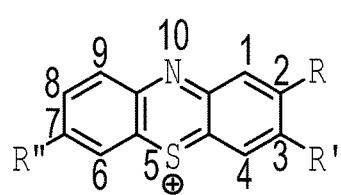
FIGS. 5A-5D depict (5A) generic structure of a cationic (oxidized) phenothiazine core structure, with ring atom numbering system in red, and R-groups (denoted R, R', and R") targeted for variation with the aim of altering the reduction potential; (5B) structural formula of PZ1; (5C) structural formula of PZ2; and (5D) structural formula of PZ9.
Figure 5B:
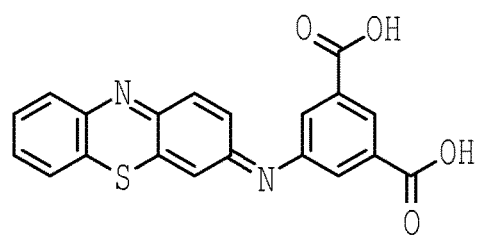
Figure 5C:
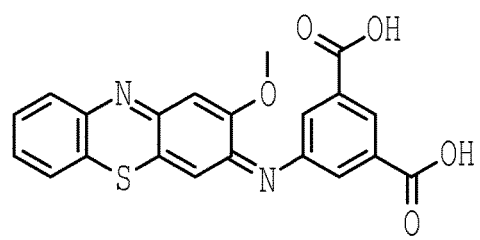
Figure 5D:
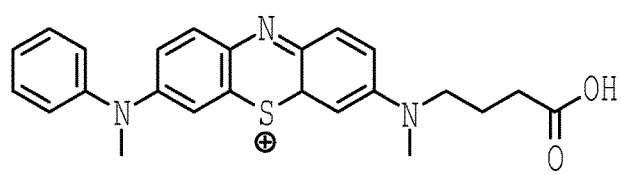

Methylene blue has been covalently attached to both Exo and Fpg oligonucleotide probes; the cleavage product for an Fpg probe is smaller than that of its Exo counterpart (FIG. 4), which may result in an increased diffusion coefficient. It should be noted that the Fpg product carries a fixed positive charge, whilst the putative Exo probe cleavage product will possess an overall negative charge at the reaction pH. MB-labelled Fpg oligonucleotide probes gave rise to a strong DPV peak signal at approximately −0.38 mV (versus a Ag/AgCl reference) in RPA reactions.

Example 2: Other Phenothiazines

Using the core phenothiazine architecture of MB as a starting point (FIG. 5), a number of redox labels (designated PZ1-11, see Table 1; note that PZ10 is carboxy-functionalized MB) were targeted for in-house synthesis and testing. Of these, three labels (PZ1, 2 and 9, FIG. 5 (b)-(d)) were attached to Fpg probes for testing in RPA.

Figure 6A:
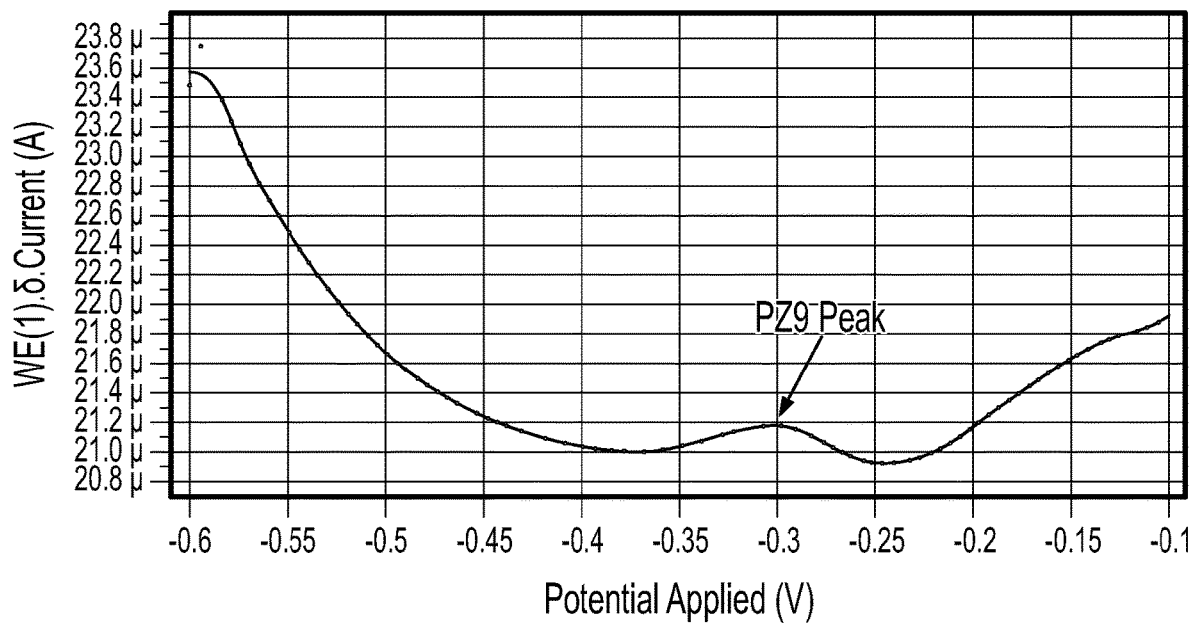
FIGS. 6A-6B depict (6A) a DPV trace illustrating the detection (at 8 min) of InfB[PA] DNA ($10^7$ copies) by RPA using a mono-labelled PZ9-labelled probe on a HeartCheck sensor; and (6B) the mean peak currents derived from a PZ9-labelled probe for NTC and positive reactions at 6 and 8 min on HeartCheck sensors. Peak currents at 1 min have been subtracted from the data shown; error bars represent ±1 SD, n=3. Positive reactions contained $10^7$ copies of target DNA.
Figure 6B:
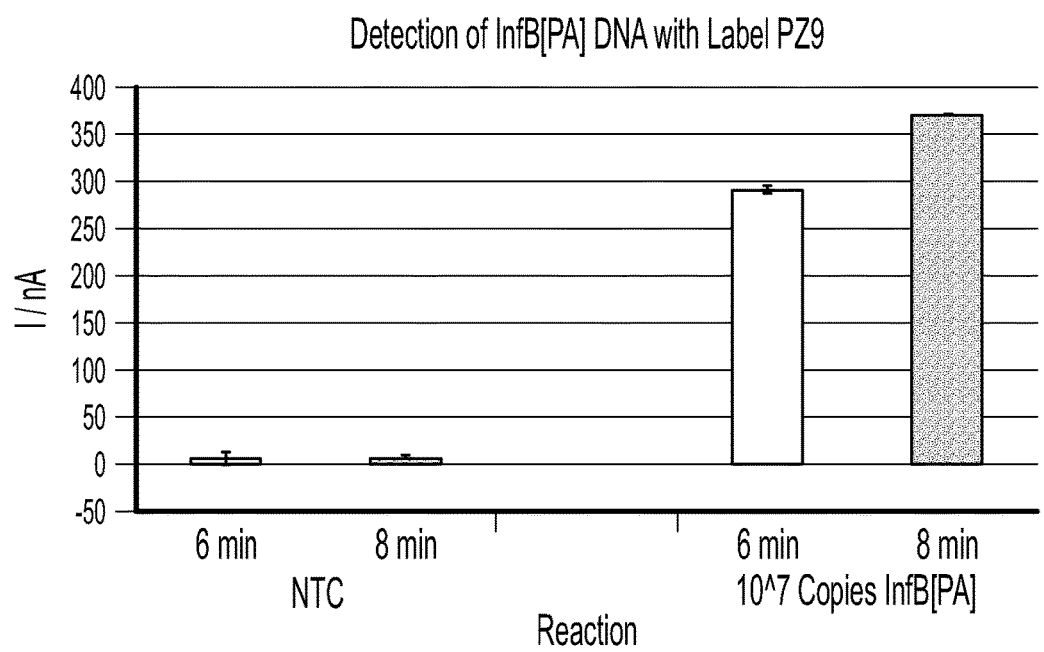
Figure 7:
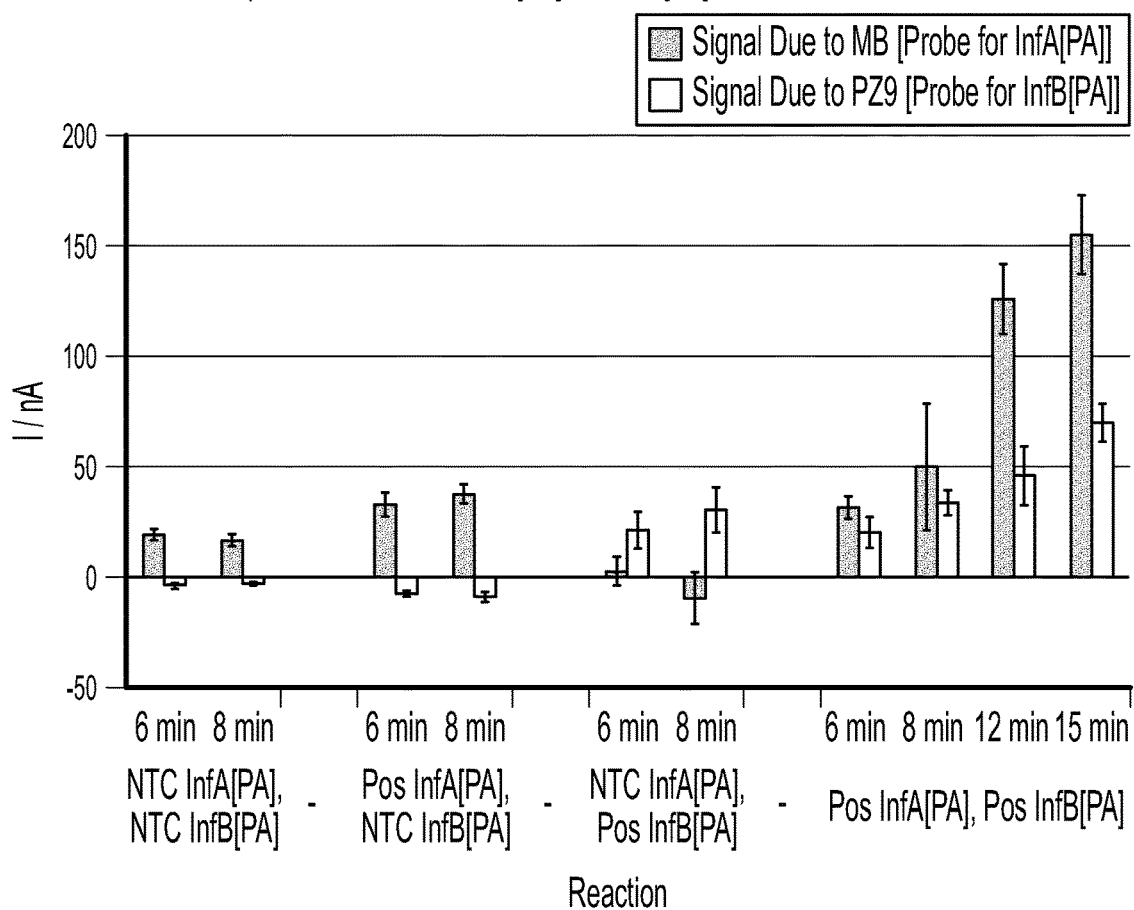
FIG. 7 depicts results of a duplexing experiment employing a 1:1 mixture of MB- and PZ9-labelled probes. Peak currents at 1 min have been subtracted from the data shown; error bars represent ±1 SD, n=3. Positive reactions contained $10^7$ copies of target DNA (the duplexed reaction contained $10^7$ copies of both targets). NTC=no template control.
Figure 8A:
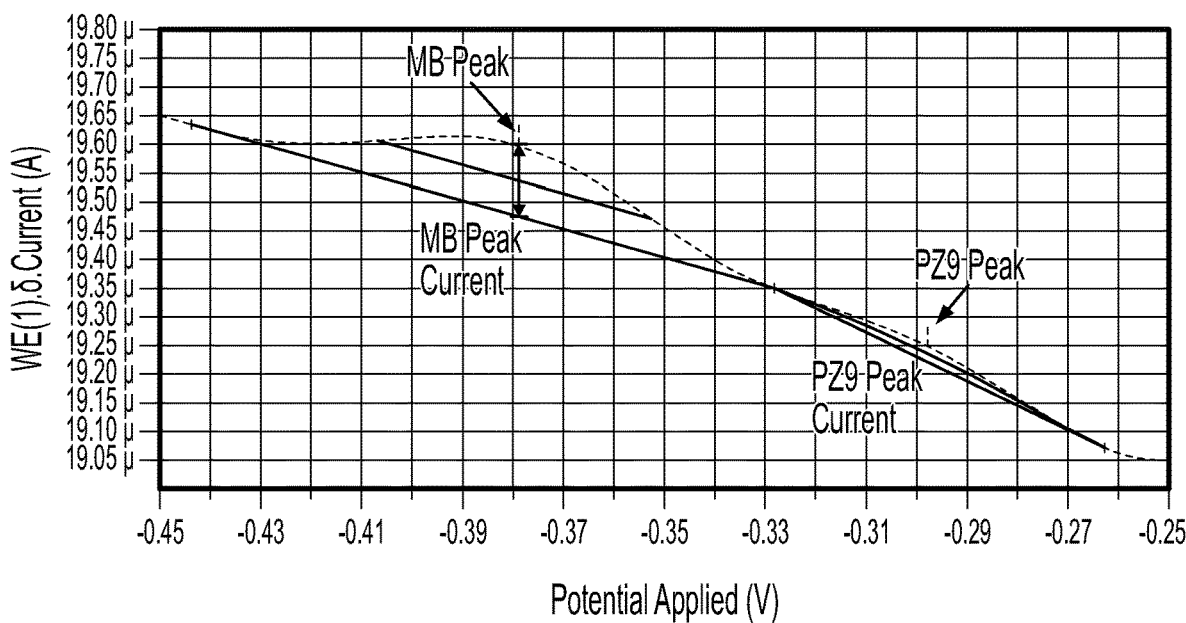
FIGS. 8A-B depict (8A) a DPV trace illustrating the duplexed detection (at 15 min) of InfA[PA] and InfB[PA] DNA ($10^7$ copies of each) by RPA using MB- and PZ9-labelled probes on a HeartCheck sensor. Shown are the linear baselines and the peak currents derived therefrom— such peak currents are used to generate the bar charts depicted in this application (following subtraction of the peak currents obtained at 1 min, e.g. see FIG. 7); and 8B) third order polynomial baseline correction of the data in (8A) yields two overlapping peaks ('Obsd' trace), which are closely modelled by the sum ('Calcd' trace) of two Gaussian curves representing the MB signal ('Calcd MB'; Emax −0.3731 V, Imax=301.5 nA, $I_{max}$=0.0311) and PZ9 signal ('Calcd PZ9'; Emax −0.3046 V, $I_{max}$=194 nA, σ=0.0243).
Figure 8B:
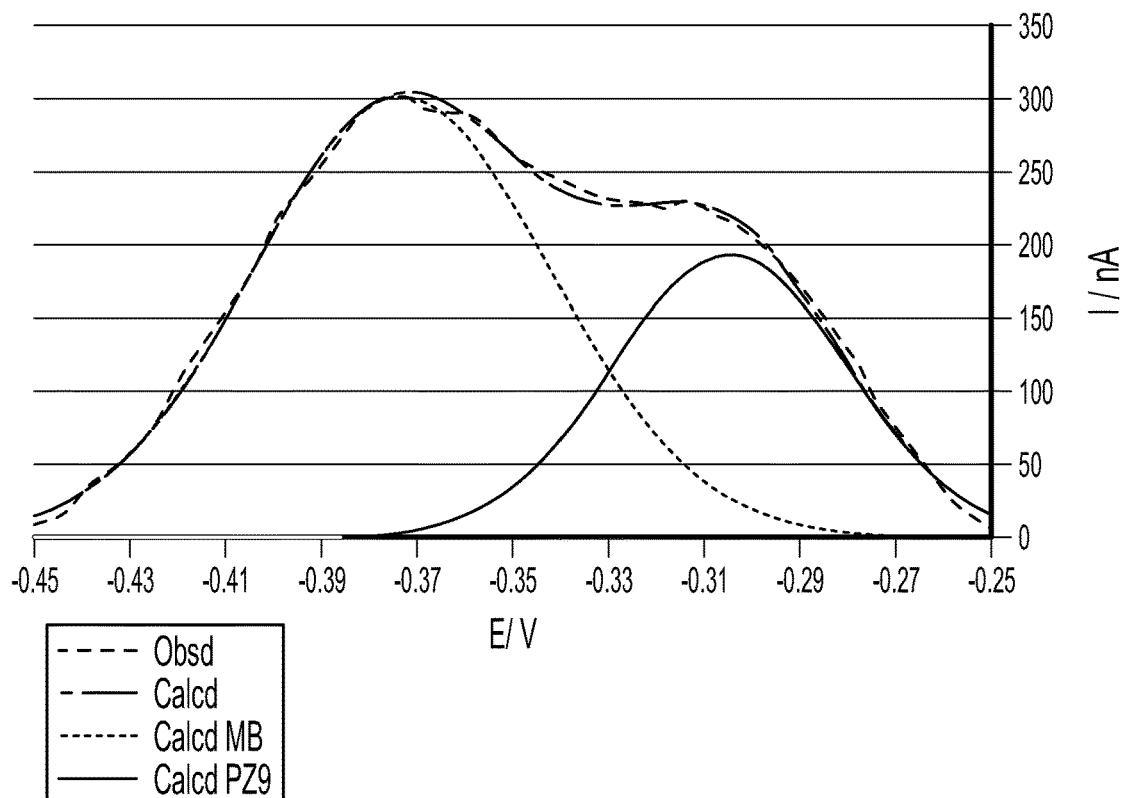
Figure 9A:
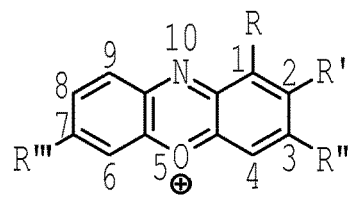
FIGS. 9A-9D depict (9A) the generic structure of a cationic (oxidized) phenoxazine core structure, with ring atom numbering system in red, and R-groups varied in this work; (9B) the structural formula of alkyl carboxy-functionalized Nile Blue, designated PO1; (9C) the structural formula of EVOblue™ 30, designated PO2; and (9D) the structural formula of PO3.
Figure 9B:
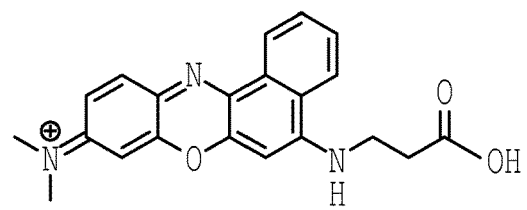
Figure 9C:
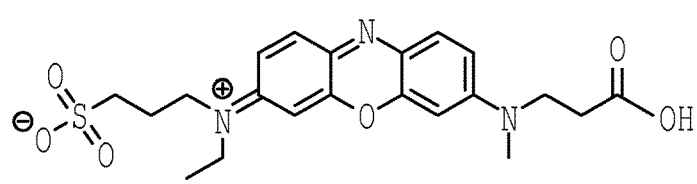
Figure 9D:
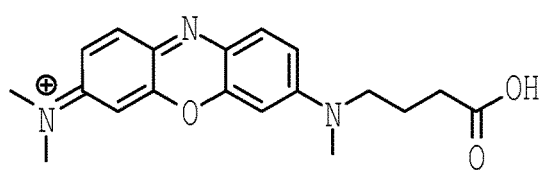

In the case of PZ1 and PZ2, both labels were successful at distinguishing between positive and NTC samples during RPA. Data obtained for PZ9 (ΔE≃+60 mV vs MB, see FIG. 6) pointed to this label as a promising candidate for sample multiplexing, and in a subsequent experiment, a model duplexed analysis of Influenza A (InfA) and Influenza B (InfB) was attempted. The results of this test confirmed PZ9 as a useful redox label for sample multiplexing; DPV analysis of a 1:1 mixture of MB-labelled InfA[PA] probe and PZ9-labelled InfB[PA] probe (both probes were mono-labelled) was able to distinguish between NTCs, samples containing InfA[PA] DNA, samples containing InfB[PA] DNA and samples containing both InfA[PA] and InfB[PA] DNA at analysis times of 6 min and beyond (see FIGS. 7 and 8)). The larger signals observed for NTC reactions devoid of any Inf DNA (i.e. reaction 'NTC InfA[PA], NTC InfB [PA]'), as compared with the NTC signals for reactions containing either InfA (i.e. 'Pos InfA[PA], NTC InfB[PA]') or InfB DNA (i.e. 'NTC InfA[PA], Pos InfB[PA]'), may be attributable to the unoptimized algorithm used for peak calling (which can be improved during development) rather than any amplification event.

Example 3: Phenoxazines

Phenoxazines represent a distinct class of redox-active organic compounds that bear a structural similarity to the phenothiazines described above. Three phenoxazine redox labels have been attached to Fpg probes and tested in RPA: Nile Blue (designated 'PO1'), EVOblue™ 30 (designated 'PO2') and 'PO3' (FIG. 9; see Table 2).

Figure 10A:
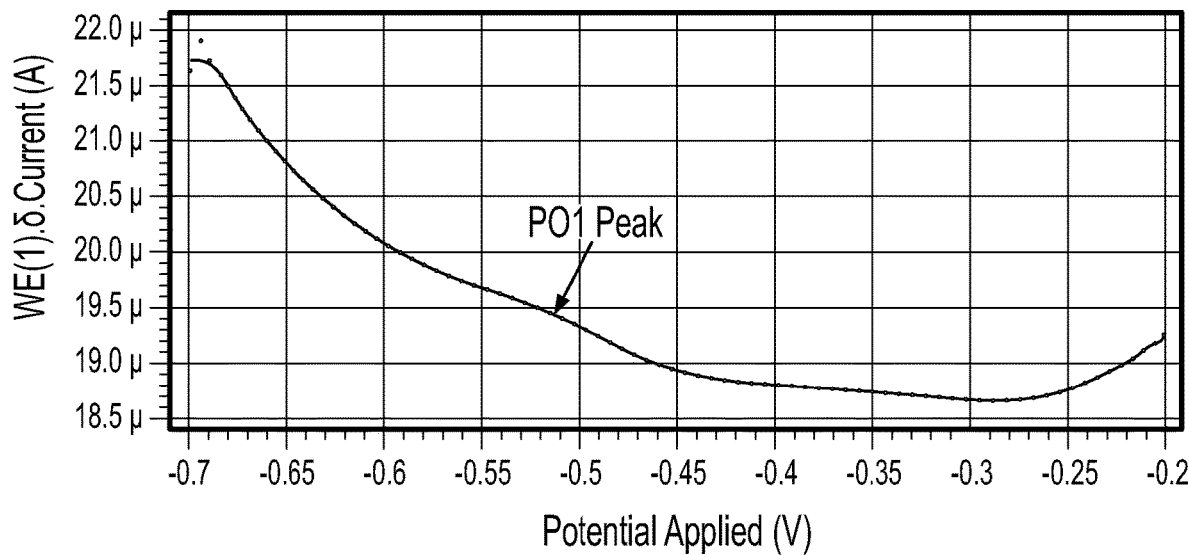
FIGS. 10A-10B depict (10A) a DPV trace illustrating the detection (at 8 min) of InfB[PA] DNA (107 copies) by RPA using a PO1-labelled probe on a HeartCheck sensor; and (10B) mean peak currents derived from a PO1-labelled probe for NTC and positive reactions at 6 and 8 min on HeartCheck sensors. Peak currents at 1 min have been subtracted from the data shown; error bars represent ±1 SD, n=3. Positive reactions contained $10^7$ copies of target DNA.
Figure 10B:
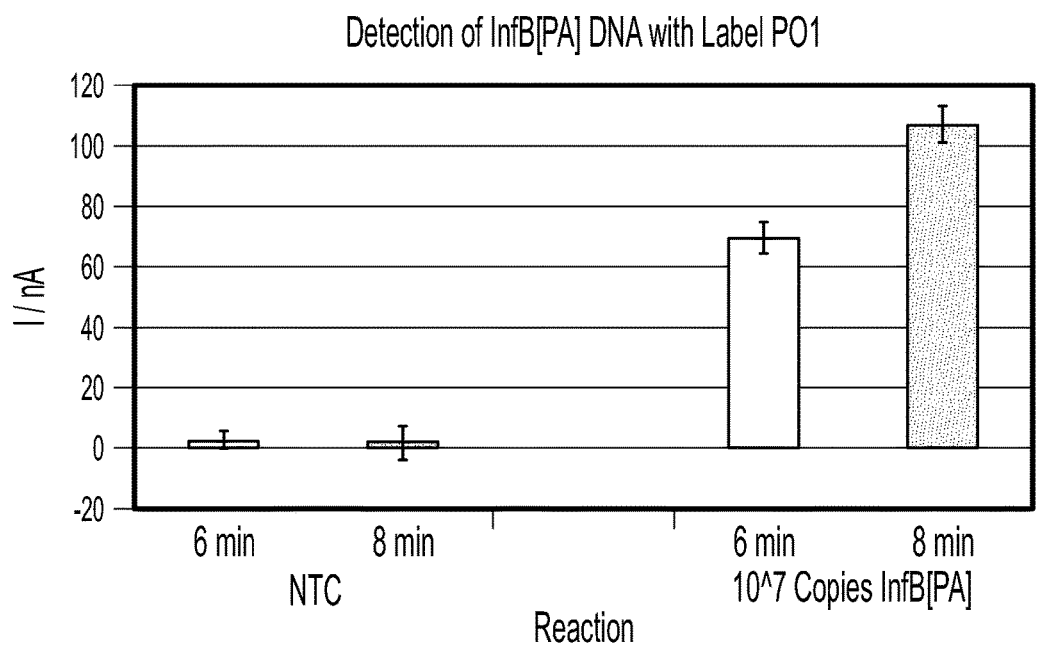

Testing demonstrated that PO1-labelled probes are able to distinguish between positive ($10^7$ copy) reactions and NTCs even after 6 min (FIG. 10). The signal generated by the label upon cleavage from the probe was well resolved from those for MB and PZ9 (E≃−0.52 V, ΔE≃−140 mV vs MB).

Figure 11A:
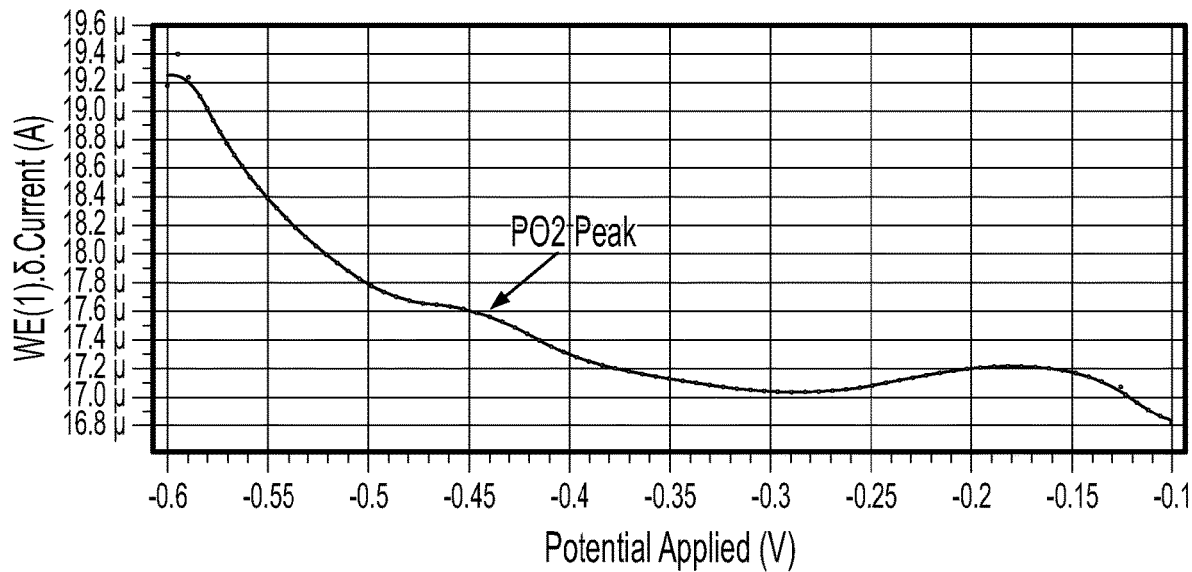
FIG. 11A-11B depicts (11A) a DPV trace illustrating the detection (at 8 min) of InfB[PA] DNA ($10^7$ copies) by RPA using a PO2-labelled probe on a HeartCheck sensor; and (11B) mean peak currents derived from a PO2-labelled probe for NTC and positive reactions at 6 and 8 min on HeartCheck sensors. Peak currents at 1 min have been subtracted from the data shown; error bars represent ±1 SD, n=3. Positive reactions contained $10^7$ copies of target DNA.
Figure 11B:
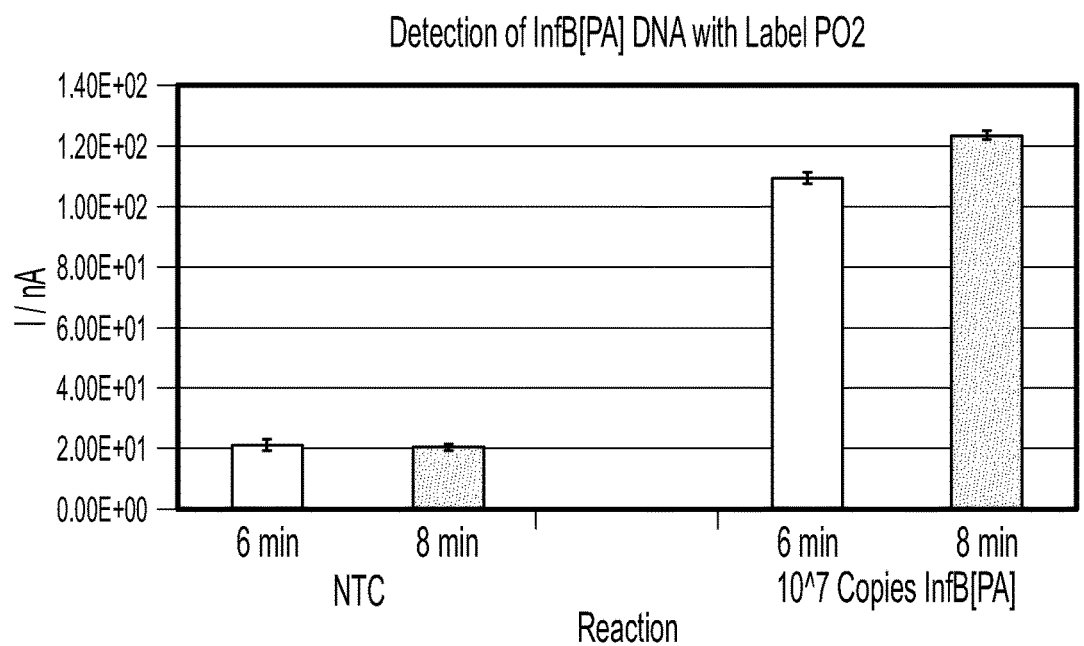

Phenoxazine derivatives PO2 displayed good aqueous solubility and a redox potential within the target window for detection; testing of an InfB[PA] Fpg probe (mono-)labelled with PO2 demonstrated that this label facilitates read-out of RPA at E≃−0.44 V (ΔE≃−60 mV vs MB). Peak current values were approximately equal to those for PO1, and thus still lower than peak currents obtained with MB (FIG. 11).

SUMMARY

Electrochemical read-out of RPA has been achieved using a total of eleven different labels (namely: MB, PZ1, PZ2, PZ9, PO1, PO2, PO3, BHQ-3, AQ-C6, [Os(bpy)2(cbpy)]2+ and di-ferrocene) representing six distinct redox-active core chemical structures (namely: phenothiazines, phenoxazines, phenazines, 9,10-anthraquinones, osmium (II) complexes and iron (II) complexes).

The Echem detection methods disclosed herein are technically compatible with multiplexed assay formats, through the application of multiple labels with redox potentials that are distinct from one another, and from background peaks arising from RPA reaction components.

Example 4: Electrochemical Detection of DNA Amplification

Figure 16:
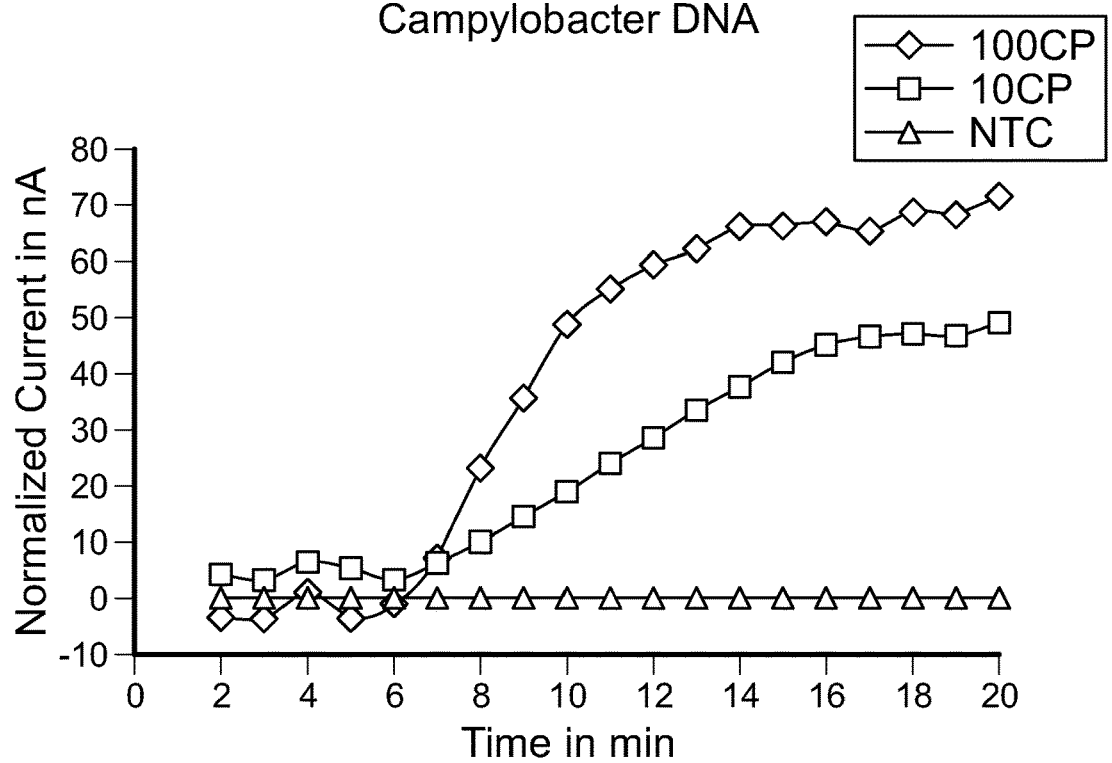
FIG. 16 depicts the electrochemical detection of amplification of *Campylobacter* DNA.
Figure 17:
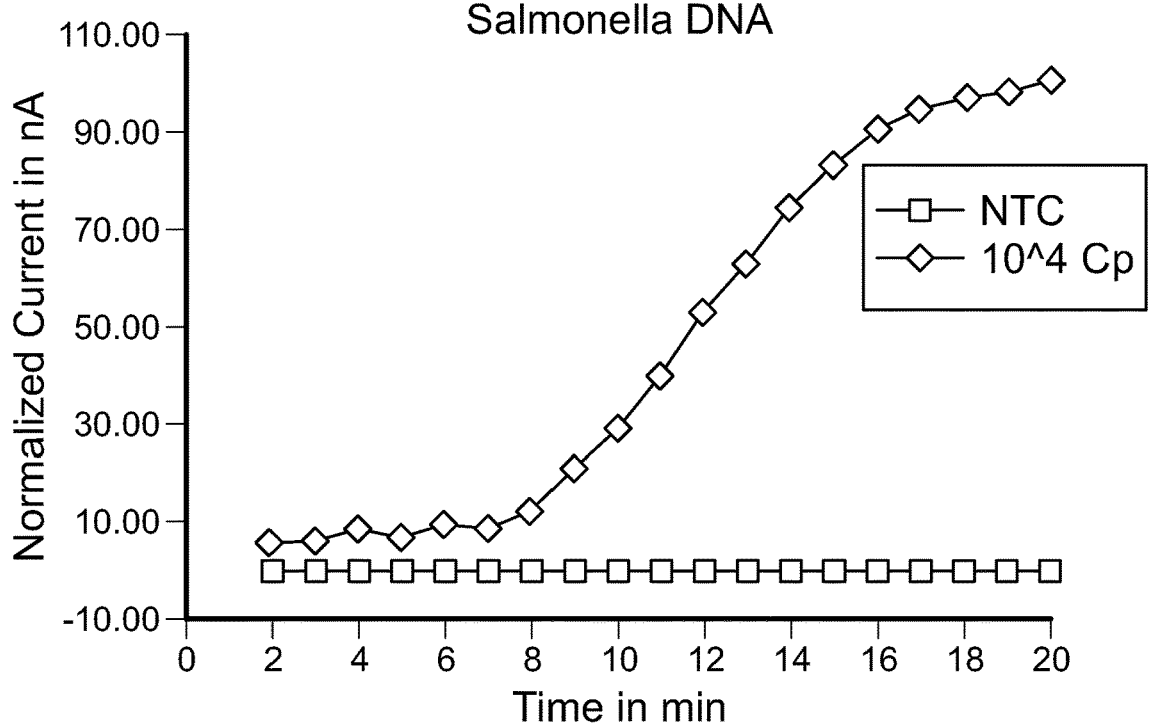
FIG. 17 depicts the electrochemical detection of amplification of *Salmonella* DNA.
Figure 18:
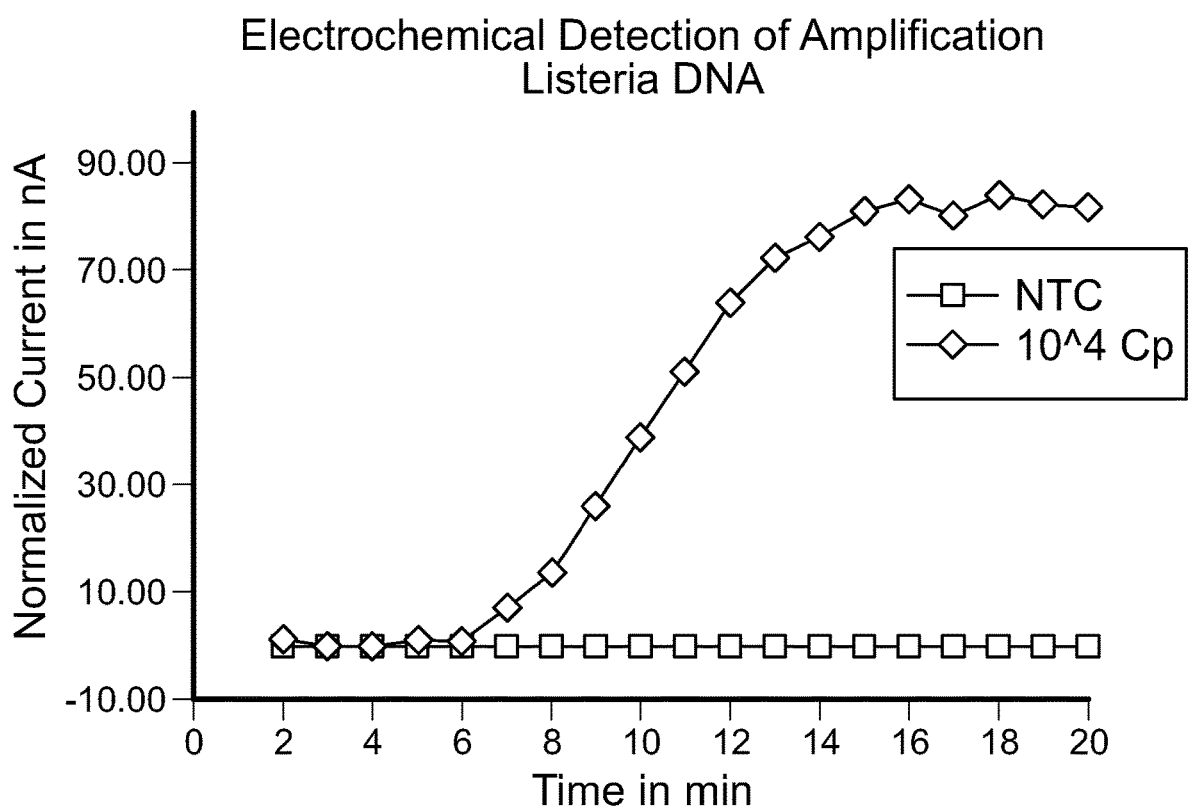
FIG. 18 depicts the electrochemical detection of amplification of *Listeria* DNA.

The signal of methylene blue released during nucleic acid amplification was measured with SPE electrode (see FIGS. 16-18). FPG solution was heated and contained equimolar amount of probe with forward and reverse primers. An algorithm was used to analyse peak height at each time point and then normalized to the baseline that was recorded with no added template (NTC). Solution was mixed during the measurement. *Campylobacter* data was measured in PCR tube (see FIG. 16) whereas *Salmonella* and *Listeria* data were measured on a custom molded card (see FIG. 17 and FIG. 18).

Each time point on each graph was derived from methylene blue (MB) peak height current obtained by single differential pulse voltammetry (DPV) sweep between −0.5V and −0.2V vs Ag/AgCl. (DPV parameters: pulse width 10 ms, step 5 mV, sweep rate 20 mV/s, amplitude 75 mV).

Sweep length is approximately 16 s where the electrode was polarized, and the electrode remained disconnected between DPV sweeps. SPE electrode area is 9 $mm^2$ with counter electrode being 10% larger. Ag/AgCl reference electrode is also screen printed and positioned in close vicinity of the working electrode.

Solution was preheated to 40° C. Reaction pellet contained premixed proteins Uvs-X UvS-Y, FPG, Pol, Tris buffer with creatine kinase, dNTP and ATP in PEG, trehalose. The freeze dried pellet was rehydrated with buffer (PEG, Tris OAc, KOAc water).

Then the rehydrated pellets of the forward and reverse primers (DNA oligomers) were added (24 nmols each per 50 uL) and the probe containing attached MB was added (24 nmol/50 uL), in the ratio of forward oligo primer/probe/reverse oligo primer (24/24/24). During the last stage, just before transferring solution into reaction chamber containing SPE electrodes, relevant DNA Template (10 copies of DNA template) was added and the reaction was initialized with MgOAc. Chamber was sealed to avoid contamination. Reaction was mixed during measurement in case of *Campylobacter* with metal ball. *Listeria* and *Salmonella* reactions were mixed at 4 min via peristaltic effect.

*Salmonella* (FIG. 17) had identical forward/probe/reverse primer ratio as *Campylobacter* (FIG. 16) (24/24/24 per 50 uL). *Listeria* (FIG. 18) had biased forward/probe/reverse primer ratio (12/24/36 nmols per 50 uL). Primer and oligonucleotide probe sequences for determination of *Campylobacter*, *Salmonella* and *Listeria* respectively were as follows:

*Campylobacter*:
Forward primer:
(SEQ ID NO: 12)
CGTGCTACAATGGCATATACAATGAGACGCAATAC;

Reverse primer:
(SEQ ID NO: 13)
CCGGCTTCATGCTCTCGAGTTGCAGAGAACAA;
and

Oligonucleotide Probe:
(SEG ID NO: 9)
AATACCGCGAGGTG[dR-methylene blue]AGCAAATCTAT[dR-methylene blue]AAATATGTCCCAGT.

*Salmonella*:
Forward primer:
(SEQ ID NO: 14)
GTGGTCCAGTTTATCGTTATTACCAAAGGTTCAG;

Reverse primer:
(SEQ ID NO: 15)
CCGTTCGCGCGCRGCATCCGCATCAATAATAC;
and

Oligonucleotide Probe:
(SEQ ID NO: 10)
ATTTTCTCTGGATG[dR-methylene blue]TATGCCCGGTAAACAGATGA[dR-methylene blue]TATTGATGCCGATT.

*Listeria*:
Forward primer:
(SEQ ID NO: 16)
CGCCTGCAAGTCCTAAGACGCCAATCGAAAAGAAAC;

Reverse primer:
(SEQ ID NO: 17)
CTGCATCTCCGTGGTATACTAATACATTGTTTTTA;
and

Probe:
(SEQ ID NO: 11)
TCGAAAAGAAACAC[dR-methylene blue]CGGATGAAATCGATAAGT[dR-methylene blue]TATACAAGGATTGG.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method comprising:
hybridizing an oligonucleotide probe to a target nucleic acid, wherein:
the oligonucleotide probe comprises an internal non-complementary or modified residue;
the internal non-complementary or modified residue is conjugated to a redox moiety; and
the redox moiety when conjugated to the internal non-complementary or modified residue does not generate a detectable electrical current in response to an electrical potential.

2. The method of claim 1, further comprising:
cleaving the oligonucleotide probe at the internal non complementary or modified residue with a nuclease, thereby providing a released redox moiety,
wherein the released redox moiety generates a detectable electrical current in response to an electrical potential.

3. The method of claim 1, further comprising amplifying a nucleic acid to produce the target nucleic acid.

4. The method of claim 3, wherein the amplifying is isothermal.

5. The method of claim 2, wherein the nuclease cleaves the oligonucleotide probe when the oligonucleotide probe is hybridized to the target nucleic acid and the nuclease does not cleave the oligonucleotide probe when the oligonucleotide probe is not hybridized to the target nucleic acid.

6. The method of claim 2, further comprising detecting an electrical current produced at a voltage corresponding to the redox potential of the released redox moiety.

7. The method of claim 2, further comprising providing an electrical potential.

8. The method of claim 1, wherein the oligonucleotide probe further comprises a 3' blocking group.

9. The method of claim 1, further comprising mixing the oligonucleotide probe, a recombinase, a polymerase, one or more nucleic acid primers, and a nuclease to provide an amplification reaction mixture.

10. The method of claim 9, further comprising adding a sample to the amplification reaction mixture.

11. The method of claim 10, further comprising obtaining the sample from a patient.

12. The method of claim 2, wherein the nuclease is an AP endonuclease, a DNA glycosylase/lyase, or a DNA glycosylase.

13. The method of claim 1, further comprising attaching the oligonucleotide probe to a solid surface.

14. The method of claim 1, wherein the internal non-complementary or modified residue comprises an abasic residue, a dSpacer, a dR-O—[C]n nucleotide, or a uracil.

15. The method of claim 1, wherein the redox moiety comprises a phenothiazine, a phenoxazine, a ferrocene, a ruthenium (II), an osmium (II), an anthraquinone, or a phenazine.

16. The method of claim 1, wherein the oligonucleotide probe is substantially complementary to the target nucleic acid.

17. The method of claim 1, wherein:
the electrical potential is between −0.25 mV and −0.55 mV.

* * * * *

SEQUENCE LISTING

```
Sequence total quantity: 17
SEQ ID NO: 1              moltype = DNA  length = 41
FEATURE                   Location/Qualifiers
misc_feature              1..41
                          note = artificial oligos
misc_feature              27
                          note = N = deoxyribonucleotide conjugated to a redox moiety
source                    1..41
                          mol_type = other DNA
                          organism = synthetic construct
SEQUENCE: 1
aagcaattga ggagtgcctg attaatnatc cctgggtttt g                          41

SEQ ID NO: 2              moltype = DNA  length = 36
FEATURE                   Location/Qualifiers
misc_feature              1..36
```

```
                        note = artificial oligos
misc_feature            21
                        note = N = deoxyribonucleotide conjugated to a redox moiety
source                  1..36
                        mol_type = other DNA
                        organism = synthetic construct
SEQUENCE: 2
gtctggctgt cagtaagtat nctagagtcc cgtttt                                36

SEQ ID NO: 3            moltype = DNA  length = 41
FEATURE                 Location/Qualifiers
misc_feature            1..41
                        note = artificial oligos
misc_feature            28
                        note = N = deoxyribonucleotide conjugated to a redox moiety
source                  1..41
                        mol_type = other DNA
                        organism = synthetic construct
SEQUENCE: 3
tcagctacaa tcaagactac tcgttaanta atgaatcctc a                          41

SEQ ID NO: 4            moltype = DNA  length = 42
FEATURE                 Location/Qualifiers
misc_feature            1..42
                        note = artificial oligos
misc_feature            28
                        note = N = deoxyribonucleotide conjugated to a redox moiety
source                  1..42
                        mol_type = other DNA
                        organism = synthetic construct
SEQUENCE: 4
gcacacttgt cacctacatt tctgattngt ggactctaac at                         42

SEQ ID NO: 5            moltype = DNA  length = 45
FEATURE                 Location/Qualifiers
misc_feature            1..45
                        note = artificial oligos
misc_feature            30
                        note = N = an abasic site mimic
source                  1..45
                        mol_type = other DNA
                        organism = synthetic construct
SEQUENCE: 5
catcagcttt tggagcttga gagtcattan gtttttgagc ttcac                      45

SEQ ID NO: 6            moltype = DNA  length = 48
FEATURE                 Location/Qualifiers
misc_feature            1..48
                        note = artificial oligos
misc_feature            33
                        note = N = an abasic site mimic
source                  1..48
                        mol_type = other DNA
                        organism = synthetic construct
SEQUENCE: 6
gaaccaagaa gcattragca aaacccaggg atnattaatc aggcactc                   48

SEQ ID NO: 7            moltype = DNA  length = 46
FEATURE                 Location/Qualifiers
misc_feature            1..46
                        note = artificial oligos
misc_feature            31
                        note = N = an abasic site mimic
source                  1..46
                        mol_type = other DNA
                        organism = synthetic construct
SEQUENCE: 7
actgatgata ttcagctaca atcaagacta ntcgttaagt aatgaa                     46

SEQ ID NO: 8            moltype = DNA  length = 38
FEATURE                 Location/Qualifiers
misc_feature            1..38
                        note = artificial oligos
misc_feature            6
                        note = N = deoxyribonucleotide conjugated to a redox moiety
misc_feature            38
                        note = N = 2',3'dideoxycytidine residue
source                  1..38
                        mol_type = other DNA
```

```
                        organism = synthetic construct
SEQUENCE: 8
acccanggat cattaatcag gcactcctca attgcttn                            38

SEQ ID NO: 9            moltype = DNA  length = 41
FEATURE                 Location/Qualifiers
misc_feature            1..41
                        note = artificial oligos
misc_feature            15
                        note = N = deoxyribonucleotide conjugated to a redox moiety
misc_feature            27
                        note = N = deoxyribonucleotide conjugated to a redox moiety
source                  1..41
                        mol_type = other DNA
                        organism = synthetic construct
SEQUENCE: 9
aataccgcga ggtgnagcaa atctataaaa tatgtcccag t                        41

SEQ ID NO: 10           moltype = DNA  length = 50
FEATURE                 Location/Qualifiers
misc_feature            1..50
                        note = artificial oligos
misc_feature            15
                        note = N = deoxyribonucleotide conjugated to a redox moiety
misc_feature            36
                        note = N = deoxyribonucleotide conjugated to a redox moiety
source                  1..50
                        mol_type = other DNA
                        organism = synthetic construct
SEQUENCE: 10
attttctctg gatgntatgc ccggtaaaca gatgantatt gatgccgatt                50

SEQ ID NO: 11           moltype = DNA  length = 48
FEATURE                 Location/Qualifiers
misc_feature            1..48
                        note = artificial oligos
misc_feature            15
                        note = N = deoxyribonucleotide conjugated to a redox moiety
misc_feature            34
                        note = N = deoxyribonucleotide conjugated to a redox moiety
source                  1..48
                        mol_type = other DNA
                        organism = synthetic construct
SEQUENCE: 11
tcgaaaagaa acacncggat gaaatcgata agtntataca aggattgg                 48

SEQ ID NO: 12           moltype = DNA  length = 35
FEATURE                 Location/Qualifiers
misc_feature            1..35
                        note = artificial oligos
source                  1..35
                        mol_type = other DNA
                        organism = synthetic construct
SEQUENCE: 12
cgtgctacaa tggcatatac aatgagacgc aatac                               35

SEQ ID NO: 13           moltype = DNA  length = 32
FEATURE                 Location/Qualifiers
misc_feature            1..32
                        note = artificial oligos
source                  1..32
                        mol_type = other DNA
                        organism = synthetic construct
SEQUENCE: 13
ccggcttcat gctctcgagt tgcagagaac aa                                  32

SEQ ID NO: 14           moltype = DNA  length = 34
FEATURE                 Location/Qualifiers
misc_feature            1..34
                        note = artificial oligos
source                  1..34
                        mol_type = other DNA
                        organism = synthetic construct
SEQUENCE: 14
gtggtccagt ttatcgttat taccaaaggt tcag                                34

SEQ ID NO: 15           moltype = DNA  length = 32
FEATURE                 Location/Qualifiers
misc_feature            1..32
```

```
                        note = artificial oligos
source                  1..32
                        mol_type = other DNA
                        organism = synthetic construct
SEQUENCE: 15
ccgttcgcgc gcrgcatccg catcaataat ac                             32

SEQ ID NO: 16           moltype = DNA  length = 36
FEATURE                 Location/Qualifiers
misc_feature            1..36
                        note = artificial oligos
source                  1..36
                        mol_type = other DNA
                        organism = synthetic construct
SEQUENCE: 16
cgcctgcaag tcctaagacg ccaatcgaaa agaaac                         36

SEQ ID NO: 17           moltype = DNA  length = 35
FEATURE                 Location/Qualifiers
misc_feature            1..35
                        note = artificial oligos
source                  1..35
                        mol_type = other DNA
                        organism = synthetic construct
SEQUENCE: 17
ctgcatctcc gtggtatact aatacattgt tttta                          35
```